US012239456B1

(12) United States Patent
Mata Magana et al.

(10) Patent No.: US 12,239,456 B1
(45) Date of Patent: Mar. 4, 2025

(54) MILLIMETER WAVE RADAR SYSTEM FOR SLEEP MONITORING

(71) Applicant: Amazon Technologies, Inc., Seattle, WA (US)

(72) Inventors: Giovanni Mata Magana, East Palo Alto, CA (US); Evan Fletcher Dougal, San Francisco, CA (US); Tianchen Li, Sunnyvale, CA (US); Alexander David Savello, San Francisco, CA (US); Ennzhi Chew, Cupertino, CA (US)

(73) Assignee: Amazon Technologies, Inc., Seattle, WA (US)

(*) Notice: Subject to any disclaimer, the term of this patent is extended or adjusted under 35 U.S.C. 154(b) by 763 days.

(21) Appl. No.: 17/224,587

(22) Filed: Apr. 7, 2021

(51) Int. Cl.
*A61B 5/00* (2006.01)
*A61B 5/08* (2006.01)

(52) U.S. Cl.
CPC .......... *A61B 5/4812* (2013.01); *A61B 5/0008* (2013.01); *A61B 5/0015* (2013.01); *A61B 5/0816* (2013.01); *A61B 2562/0271* (2013.01); *A61B 2562/16* (2013.01); *A61B 2562/166* (2013.01)

(58) Field of Classification Search
CPC ... A61B 5/4812; A61B 5/0008; A61B 5/0015; A61B 5/0816; A61B 2562/0271; A61B 2562/16; A61B 2562/166
See application file for complete search history.

(56) References Cited

U.S. PATENT DOCUMENTS

| | | | | |
|---|---|---|---|---|
| 10,568,565 B1 * | 2/2020 | Kahn | ............... | A61B 5/1126 |
| 11,184,738 B1 * | 11/2021 | Rigazio | ............... | H04W 4/80 |
| 11,374,311 B2 * | 6/2022 | Yamada | ............... | H01Q 1/422 |
| 2016/0344393 A1 * | 11/2016 | Kawano | ............... | G01S 7/352 |
| 2020/0295452 A1 * | 9/2020 | Yamada | ............... | G01S 13/931 |
| 2021/0183797 A1 * | 6/2021 | Vincent | ............... | H01P 11/002 |
| 2021/0184340 A1 * | 6/2021 | Stav | ............... | G01S 13/931 |
| 2022/0094048 A1 * | 3/2022 | Wu | ............... | H01Q 19/005 |

FOREIGN PATENT DOCUMENTS

WO   WO-2021067860 A1 *   4/2021   .......... A61B 5/0008

* cited by examiner

*Primary Examiner* — Rochelle D Turchen
(74) *Attorney, Agent, or Firm* — Kilpatrick Townsend & Stockton LLP

(57) ABSTRACT

Systems and methods relating to a millimeter wave radio-frequency (RF) sleep monitoring device are described. The device includes a surface transparent to RF signals through which a radar device enclosed in a housing transmits RF signals. An antenna array is enclosed within the housing and is oriented at a non-zero angle with respect to a vertical axis of the device. The antenna array receives the reflected RF signals through the surface. The reflected RF signals are used to generate sleep monitoring data such as a respiratory rate or motion data associated with a user.

21 Claims, 16 Drawing Sheets

MILLIMETER WAVE RADAR SYSTEM FOR SLEEP MONITORING

BACKGROUND

Health improvements can be achieved by monitoring how a user sleeps. Different technologies have been proposed for sleep monitoring. In a common approach, sensors are attached to the user. However, this approach can interfere with the user's ability to sleep and, thus, may have an adverse health effect. In another approach, audio and/or video sensors are used. Although less intrusive, this approach raises privacy concerns. In yet another approach, motion sensors, such as gyroscopes and magnetometers in a smart phone, are placed on the sleeping surface. Here, the accuracy of the sleep monitoring can be less than optimal.

BRIEF DESCRIPTION OF THE DRAWINGS

Various embodiments in accordance with the present disclosure will be described with reference to the drawings, in which.

DETAILED DESCRIPTION

Figure 1:
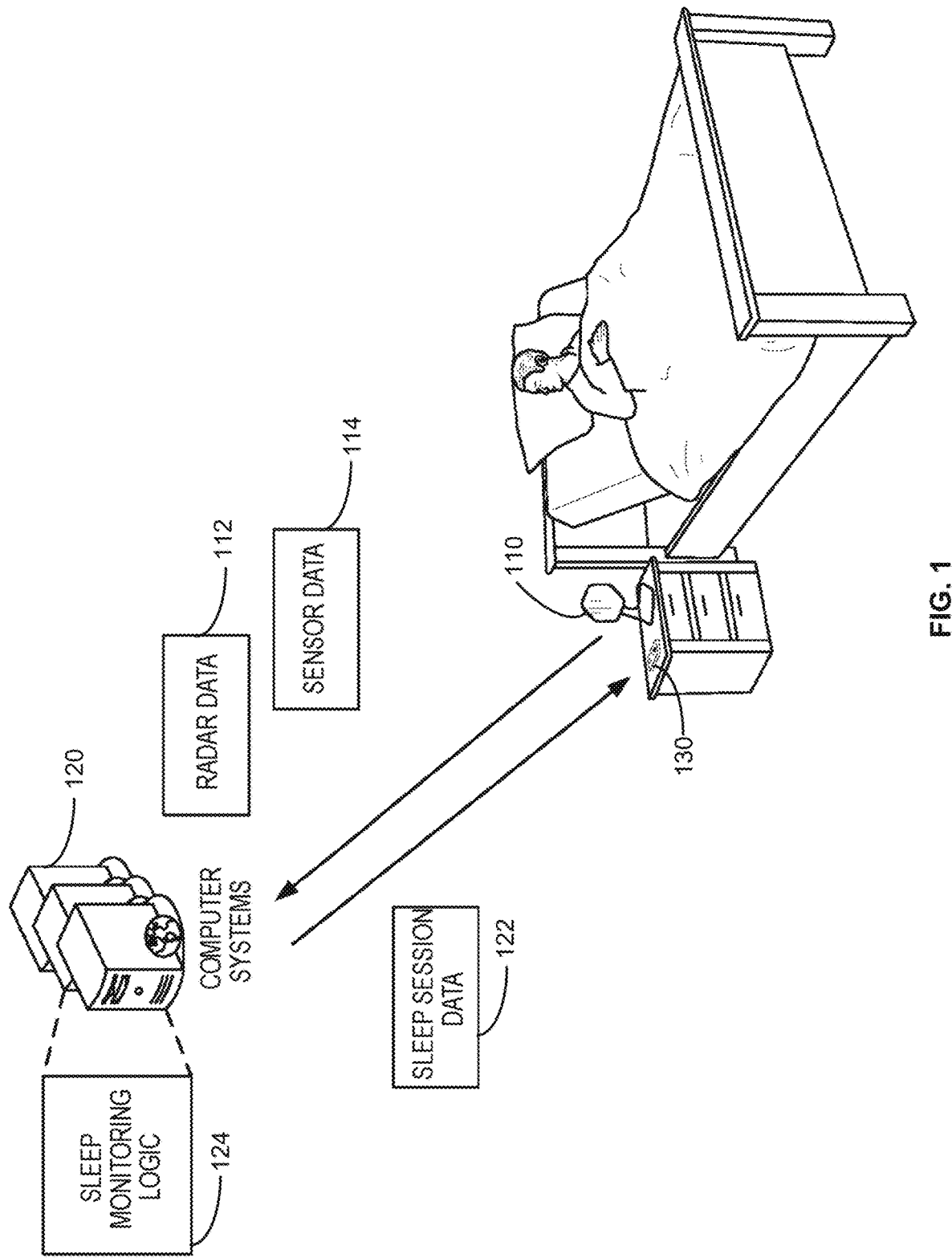
FIG. 1 illustrates an embodiment of a computing environment for sleep monitoring.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Embodiments of the present disclosure relate to, among other things, sleep monitoring based on millimeter wave (mmwave) radio frequency (RF) signals. In some embodiments, a sleep monitoring device transmits mmwave RF signals in an environment and receives mmwave RF signals reflected from a target in the environment. The received mmwave RF signals are processed to generate radar data related to the target's sleep. In some embodiments, the radar data can include macro-level data related to motion of the target and micro-level data related to the respiratory rate of the target. The sleep monitoring device can also include a set of sensors to generate data related to the environment, such as ambient light, humidity, and/or temperature. The radar data and the sensor data can be send to a remote computer system that executes logic for fusing the different data and generating sleep monitoring data. The sleep monitoring data can include data about, for instance, different sleep stages of the target, including rapid eye movement (REM), light, deep, and awake stages. The computer system can send the sleep monitoring data to a user device of the target.

The use of mmwave RF signals for sleep monitoring provides several technological advantages over existing sleep monitoring system. In some embodiments, this use is not intrusive to the target. Further, because no audio or video sensors are needed, the target's privacy is significantly improved. Additionally, mmwave RF signals enable macro-level detection of motion such that the radar data can be latched to and the sleep monitoring can tracked for a particular target. The mmwave RF signals also enable micro-level detection of motion of the target, such as chest displacement, through different materials between the target and the sleep monitoring device (e.g., bed sheets that may cover the target). The macro-level and micro-level detections significantly improve the accuracy of the sleep monitoring.

To illustrate, consider an embodiment of a sleep monitoring device that is portable. The sleep monitoring device includes a stand and a housing connected therewith. The housing includes a radome transparent to mmwave RF signals and a mmwave radar chip (also referred to herein as a mmwave radar device) that includes a set of antennas. The mmwave radar chip is at a predefined distance away from the radome, such as about 1.8 mm when the RF frequency is in the 60 GHz range, to optimize the transmission and reception of mmwave RF signals. In some embodiments, the predefined distance may be greater than 1.7 mm when the RF frequency is in the 60 GHz range. When other frequencies of RF signals are used, the predefined distance may be greater than or less than 1.8 mm based on a minimum distance required by the radar device for a gap between the radar device and the radome. Further optimization can be achieved by installing the mmwave radar chip is installed in the housing at a non-zero angle relative to the vertical axis. In some embodiments, the housing further includes one or more processors, that may for example be embodied in one or more processing chips (e.g., one or more microcontrollers or CPUs) and a connectivity chip (e.g., a Wi-Fi, Bluetooth 5.0, or similar chip that supports wireless communication protocols) that provides for communications between the sleep monitoring device and one or more external computing devices (the one or more processors and the connectivity chip are also referred to herein as a processing device and a connectivity device, respectively), a an input mechanism (e.g., a button, microphone, capacitive touch sensor, and other such devices that can receive an input), a first set of sensors to detect environmental data, such as a temperature sensor, a humidity sensor, and an ambient light sensor, and a second set of position sensors to detect a position of the sleep monitoring device, such as a gyroscope and a magnetometer. The one or more processors are coupled with these various components.

In operation, the sleep monitoring device can be placed, by using the stand, on a nightstand next to a user's bed and oriented towards the bed. Position data generated by the second set of sensors can be used to properly position and orient the sleep monitoring device such that the bed is in the RF field of view of this device. Upon a trigger event to start a sleep session (e.g., an activation of the input mechanism via pressing a button, uttering a voice command, or otherwise inputting a signal to trigger the sleep session or instruction data from a cloud computing service received via the connectivity chip), the one or more processors, for example as embodied in the processing chip can activate the mmwave radar chip. mmwave RF signals are transmitted and reflected mmwave RF signals are received. The mmwave RF chip generates radar data based on the received mmwave RF signals, where the radar data indicates motion data and/or respiratory rate data, among other things. The one or more processors receive the radar data from the mmwave radar chip and sensor data from the first set of sensors and buffers the received data. Periodically, the buffered data is sent to the cloud computing service for sleep monitoring analysis. The derived sleep monitoring data can then be sent to a user device, such as a smartphone.

FIG. 1 illustrates an embodiment of a computing environment for sleep monitoring. As illustrated, the computing environment includes a sleep monitoring device 110, a computer system 120, and a user device 130. The sleep monitoring device 110 can be positioned in a space within a physical environment (such as by being placed on a nightstand in a bedroom). The sleep monitoring device 110 is communicatively coupled with the computer system 120 over a data network, such as one that includes the Internet. The computer system 120 is also communicatively coupled with the user device 130. A direct data connection need not exist between the sleep monitoring device 110 and the user device 130. Instead, the computer system 120 can facilitate communications between the sleep monitoring device 110 and the user device 130.

In an embodiment, the sleep monitoring device 110 implements mmwave RF technology to generate and send radar data 112 to the computer system 120. At a start of a sleep session, the sleep monitoring device 110 can transmit mmwave RF signals (e.g., in the range of thirty to three-hundred GHz, such as around sixty GHz). The reflected mmwave RF signals are received and processed into the radar data 112, where this radar data 112 indicates macro-level motion (e.g., a motion of a target on a bed in the space) and micro-level motion (e.g., a displacement of the target's chest indicating a respiratory rate). The radar data 112 may be generated at a particular data rate, such as every one hundred milliseconds. The sleep monitoring device 110 can also include a set of sensors that generate sensor data 114 related to the space. The sensor data 114 can be sent to the computer system 120. The sending of the radar data 112 and the sensor data 114 can be periodic at a particular transmission rate, such as every five minutes, to constitute a data stream from the sleep monitoring device 110 to the computer system 120. In some embodiments, the radar data 112 and the sensor data 114 may be transmitted asynchronously, e.g., the radar data may be transmitted every five minutes while sensor data 114 may be transmitted every thirty minutes.

Embodiments of computing components of the sleep monitoring device 110 are further illustrated in the next figures.

The computer system 120 can be implemented as a set of hardware (e.g., a set of servers) or a set of virtualized computing services (e.g., a cloud computing service) on computing hardware. The computer system 120 receives the radar data 112 and the sensor data 114 from the sleep monitoring device 110 and processes this data to generate, among other things, sleep session data 122. To do so, the computer system 120 hosts a sleep monitoring module 124 that analyzes the radar data 112 and the sensor data 114 over time. Different analysis techniques are possible. In one embodiment, a fusion algorithm is used to fuse the sensor data 114 together and/or to fuse the radar data 112 and the sensor data 114. Further, a machine learning (ML) model can be trained to detect sleep stages based on input data, where the input data corresponds to the output of the fusion algorithm. Statistical analysis can be performed to determine, for instance, average time or some other metrics per sleep stage. Pattern detection and plotting algorithms can be used to detect and illustrate patterns from the metrics and/or from the radar data 112 and the sensor data 114 (e.g., to show respiratory rate change per sleep stage, and the average temperature of the space during the sleep stage). This different application modules can be components of the sleep monitoring module 124. Some or all of the output data of the application modules can be included in the sleep session data 122 depending on, for example, user preferences and settings.

The user device 130 can receive can present the sleep session data 122. In some embodiments, the sleep session data 122 may be available to the user device 130 upon completion of a session. In some embodiments, portions of the sleep session data 122 (e.g., metrics about respiratory rate or respiratory waveforms) can be received in real-time relative to when the computer system 120 generates and sends these portions. Other portions of the sleep session data 122 can be sent upon an end of the sleep session. And remaining or all portions of the sleep session data 122 can be made available upon demand from the user device 130.

Although the user device 130 is illustrated as being in the same space (e.g., the bedroom) as the sleep monitoring device 110, embodiments of the present disclosure are not limited as such. Generally, the user device 130 can be any type of computing device available to a user and suitable for communicating with the computer system 120 and presenting the sleep session data 122. For instance, the user device 130 can be a smart phone, a tablet, a laptop, a desktop, a smart speaker, a wearable device, a smart appliance, an internet of things (IoT) device, or any other type of computing device.

The computing environment of FIG. 1 can include other components that can subscribe to, use, or be controlled based on some or all portions of the sleep session data 122. For example, the physical environment can be equipped with smart devices (e.g., a smart home that incudes smart speakers, smart lights, smart locks, a smart security system, and/or other devices that can be remotely controlled). The computer system 120 can use the sleep session data 122 as in a feedback loop to control such smart devices. For instance, depending on a detected sleep stage, the computer system 120 can instruct a smart speaker located in the space to stream and play particular audio (e.g., white noise), a smart light located in the space to change color or dim to a certain level of brightness, a smart lock of the physical environment to lock or unlock, and/or a security system to arm or disarm.

Variations to the above computing environment are also possible. For example, some or all of the functionalities of the sleep monitoring module 124 can be implemented on the user device 130 (in which case, the computer system 120 need not be included in the computing environment) and/or distributed between the computer system 120 and the user device 130. Additionally or alternatively, some or all of the sleep monitoring functionalities of the user device 130 (e.g., to receive and present the sleep session data 122) can be implemented on the sleep monitoring device 110. In yet another variation, the sleep monitoring device 110 can implement the relevant functionalities of the computer system 120 and the user device 130 (in which case, the computer system 120 and the user device need not be included in the computing environment).

Figure 2:
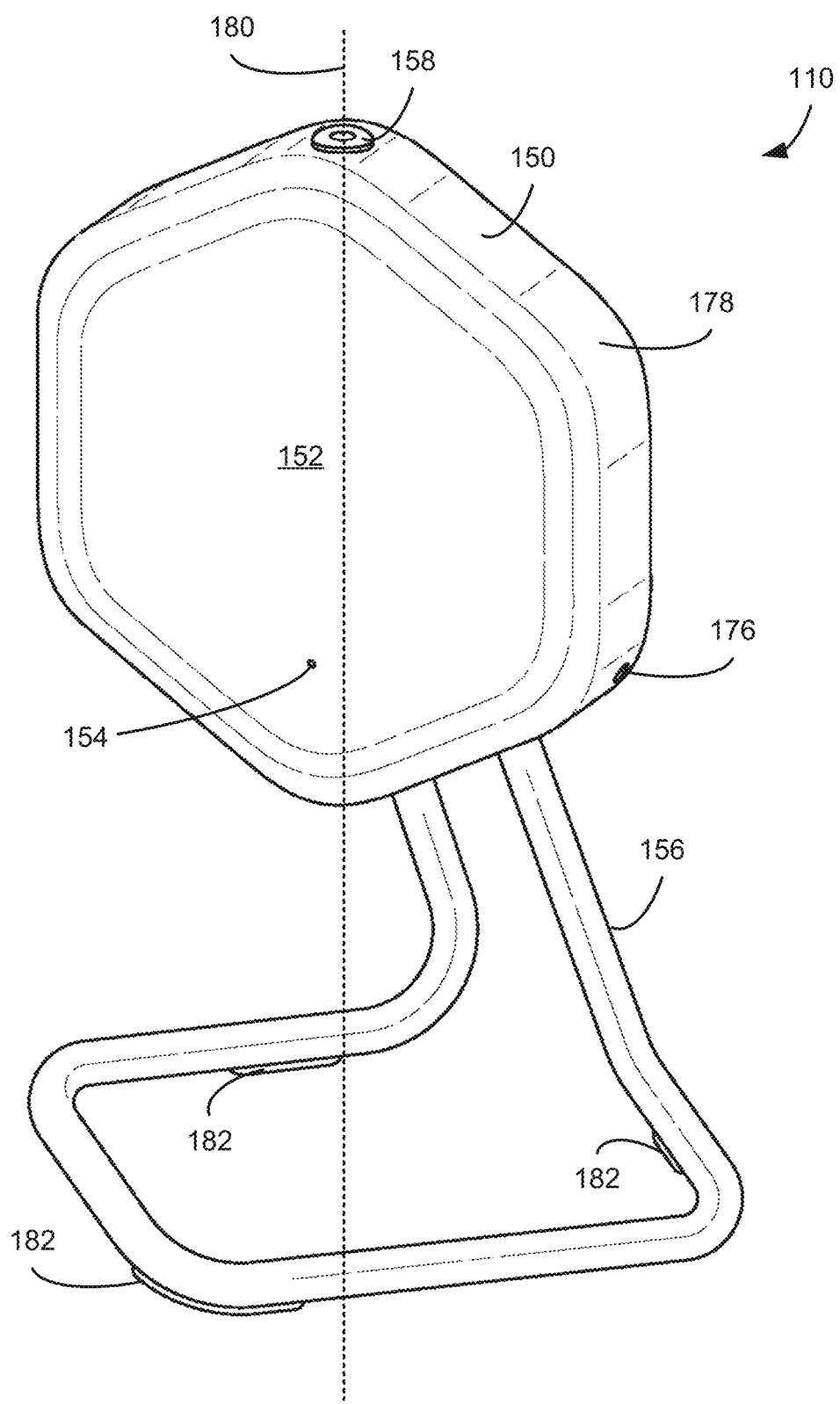
FIG. 2 illustrates a perspective view of an embodiment of a sleep monitoring device.

FIG. 2 illustrates a perspective view of an embodiment of a sleep monitoring device. As illustrated, the sleep monitoring device 110 is shown with a housing 150 and stand 156 to support the housing 150. The sleep monitoring device 110 can be positioned in a space within a physical environment (such as by being placed on a nightstand in a bedroom). The housing 150 encloses components for performing processes described herein, such as the processes described with respect to FIGS. 8 and 9. The sleep monitoring device 110 is communicatively coupled with a computer system, e.g., computer system 120 over a data network, such as one that includes the Internet or over a local network such as a BLUETOOTH connection. In some embodiments, a direct data connection may exist between the sleep monitoring device 110 and a computer system, such as the user device 130 or computer system 120.

The sleep monitoring device 110 is supported by a stand 156 that rests on a supporting surface. The stand 156 extends along a vertical axis 180, which may be parallel to a vertical axis of the housing 150, e.g., from the top to the bottom of the housing 150. The stand 156 is a wire frame stand that connects to the housing 150 as shown and described with respect to FIG. 5. The wire frame may include a rigid or semi-rigid core covered or coated with a second material. The rigid core may provide strength and support while the second material provides for an aesthetic look and feel, such as to cushion the stand 156. The stand 156 includes feet 182 to resist slipping and movement of the stand 156 against a supporting surface. The feet 182 may be rubber feet that provide for an increased coefficient of friction between the stand 156 and the supporting surface to resist movement of the sleep monitoring device 110.

Figure 4:
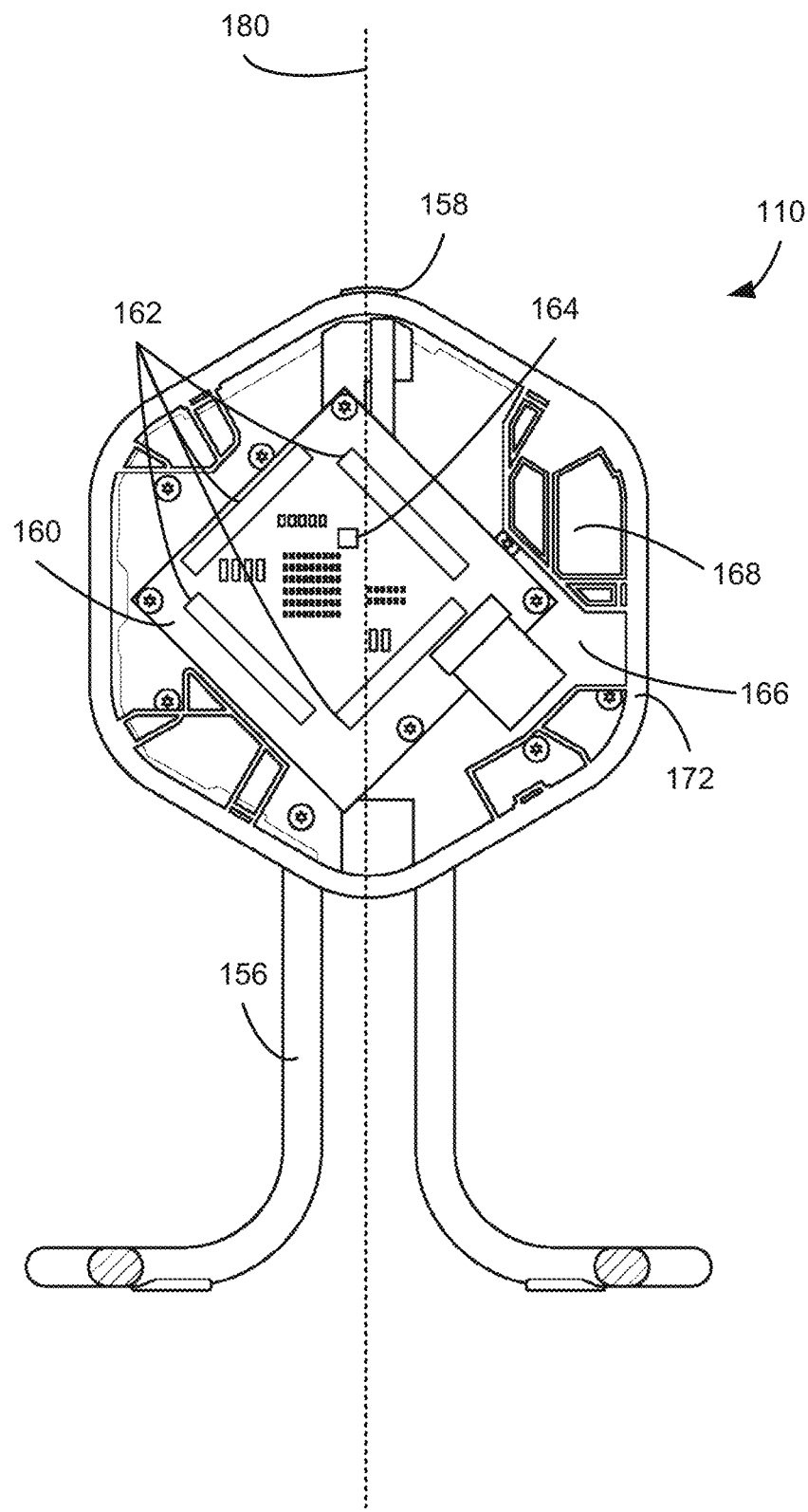
FIG. 4 illustrates an embodiment of an installation of a millimeter wave radar chip in a housing of a sleep monitoring device.

The housing 150 has a hexagonal shape at an outer perimeter, to accommodate radar components as shown and described with respect to FIG. 4, while maintaining a small profile and thereby remaining unobtrusive. The housing 150 is formed of several components, including a front surface 152, a perimeter 178, and a back surface (not shown). The components of the housing 150 are assembled together and may be formed of a plastic, metal, composite, or any other suitable structural material. In some embodiments, the housing 150 may be assembled of additional components or may be formed as a unibody shell with an access panel to provide access to an interior of the housing 150. The perimeter 178 and back panel may each be formed of a material that is non-RF transparent material. In some embodiments, the housing 150 may be assembled without threaded connections or fasteners, and may instead rely on clips, frictional engagements, and other such fastenerless assembly devices.

The front surface 152 acts as a radome for the radar device stored within the housing 150 such that the radar device is protected while also enabling transmission of RF waves through the front surface. The front surface 152 is transparent to RF signals, particularly to millimeter wave RF signals such as are emitted from the sleep monitoring device 110. The front surface 152 may be permanently joined with the perimeter 178 or may be removable from the housing 150. The front surface 152 may be composed of a single piece or may be formed of multiple segments or parts. The front surface 152 is flat, but may, in some embodiments, have a dome-like shape extending from the housing 150. In some embodiments, the housing 150, with the exception of the front surface 152, may block RF signals to prevent interference and noise from other potential sources.

The housing 150 includes an indicator light pipe 154, input mechanism 158, and sensor port 176. The indicator light pipe 154 provides for light signals to be emitted from within the housing through the front surface 152, for example to provide feedback or information to a user regarding an operational status of the sleep monitoring device 110. The indicator light pipe 154 may be positioned around the perimeter 178, on the back, or any other position on the housing 150. The input mechanism 158 is shown as a button positioned at the top end of the housing 150 and enables a user to interact with the sleep monitoring device 110, such as to initiate a cycle or process, including as described with respect to FIGS. 6, 8, and 9. In some embodiments, the activation button 158 may include additional components, such as an indicator light to emit light in a manner similar to the indicator light pipe 154, and an ambient light sensor to gather data relating to a level of ambient light in the environment surrounding the sleep monitoring device 110. The data from the ambient light sensor may be sent to a processing device enclosed within the housing 150 for processing as well as communication with other devices outside of the housing 150. The sensor port 176 provides an access port for exchange of atmosphere between the inside and outside of the housing 150. One or more sensors positioned within the sensor port 176 may be used to gather data relating to temperature, humidity, and other environmental conditions to be conveyed to the processing device within the housing.

Figure 3:
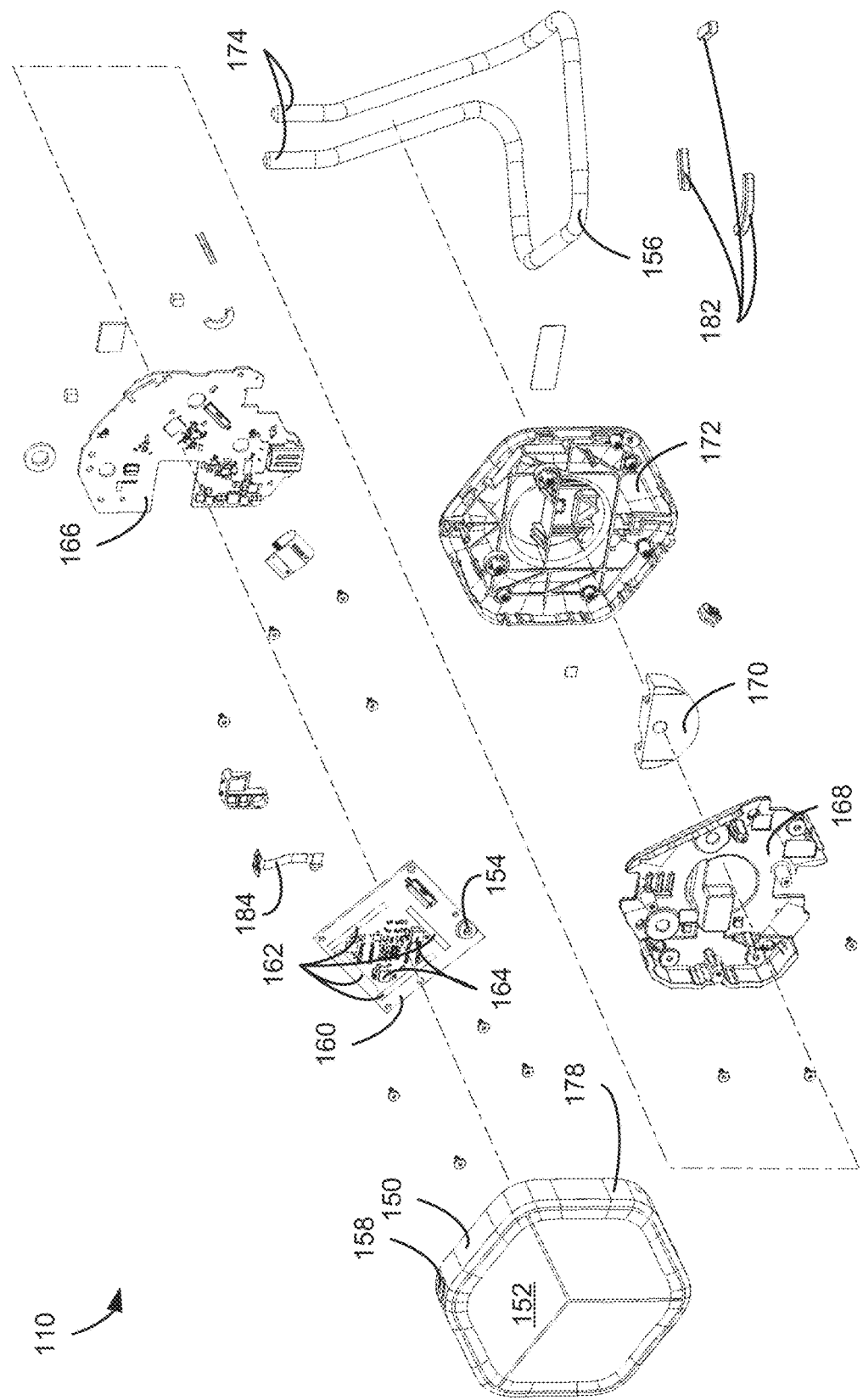
FIG. 3 illustrates an exploded view of an embodiment of a sleep monitoring device.

FIG. 3 illustrates an exploded view of an embodiment of a sleep monitoring device. The sleep monitoring device 110 includes components described above with respect to FIG. 2 including the front surface 152, housing 150, perimeter 178, input mechanism 158, indication light pipe 154, stand 156, and feet 182. When disassembled in the exploded view of FIG. 3, the components stored within housing 150 are visible and include a millimeter wave radar chip 160, processor board 166, heat sink 168, stand clamp 170, and back surface 172.

The millimeter wave radar chip 160 includes components for transmitting and receiving RF signals through the front surface 152. The millimeter wave radar chip 160 is shown as a chip including components for transmitting, receiving, processing, and conveying RF signals and data corresponding thereto. The millimeter wave radar chip 160 also includes the indication light pipe 154, or a portion thereof, that may be visible through the front surface 152. The millimeter wave radar chip 160, when assembled, is positioned adjacent the front surface 152 without any intervening surfaces or objects to obscure RF signals. The millimeter wave radar chip 160 is positioned close to the front surface 152, for example at a range of one to three millimeters from the front surface 152 or less. In some embodiments, the millimeter wave radar chip 160 may be positioned at a distance of about 1.8 millimeters from the front surface 152. The millimeter wave radar chip 160 can support functionalities of a radar signal emitter by, for instance, including one or more emitters 164 for transmitting RF signals outward through the front surface 152. The emitters may transmit RF signals of millimeter wave size, though other sizes of waves and types of emitters are envisioned as compatible. The millimeter wave radar chip 160 also includes an antenna array 162 including multiple antenna receivers. The antenna array 162 is arranged such that the array is not aligned with the vertical axis of the housing 150, e.g., the antenna array 162 is not parallel or perpendicular to the axis 180 of FIG. 2. The antenna array 162 is arranged at an angle of between thirty and sixty degrees with respect to the vertical axis. The non-zero angle relative to the vertical axis enables the antenna array to receive RF signals and reduces the impact of signal strength fluctuations due to polarization angle differences and multi-path cancellation of RF signals. The antenna array 162, and any other components connected to the antenna array or the millimeter wave radar chip 160 are coupled to the processor board 166 via a flexible connection 184 that provides a communicative connection between the millimeter wave radar chip 160 and the processor board 166. In some examples, the antenna array 162, or other components of the millimeter wave radar chip 160 may be included on other structures or devices besides the millimeter wave radar chip 160 shown in FIG. 3, for example with the antenna array disposed on a separate chip or device.

The processor board 166 is positioned on the opposite side of the millimeter wave radar chip 160 from the front surface 152, e.g., towards the back of the housing 150. The processor board 166 may include one or more CPUs, microcontrollers, connectivity devices, and other such elements. The processor board 166 is communicatively coupled with the millimeter wave radar chip 160 such that operation of the radar device may be controlled by the processor board 166 and data may be sent from the millimeter wave radar chip 160 to the processor board 166. The processor board 166 may include one or more processors and circuit elements, such as application-specific integrated circuits and other such elements, including communication devices for communicating with other elements within the housing 150 as well as outside the housing 150, including the user device 130 and the computer system 120.

The heat sink 168 is positioned towards the back of the housing 150 from the millimeter wave radar chip 160 and may be connected to each of the millimeter wave radar chip 160 and the processor board 166. The heat sink 168 may be positioned behind, towards the back of the housing 150, the processor board 166 or may be in between the millimeter wave radar chip 160 and the processor board 166. The heat sink transfers heat from the millimeter wave radar chip 160 and the processor board 166 and dissipates the heat to the surrounding environment. The heat sink 168 is sized and shaped to occupy a substantial fraction of the interior of the housing 150 and includes fins and structures for connecting the millimeter wave radar chip 160 and processor board 166 as well as to connect to the interior of the housing 150 and dissipate heat as efficiently as possible.

Figure 5:
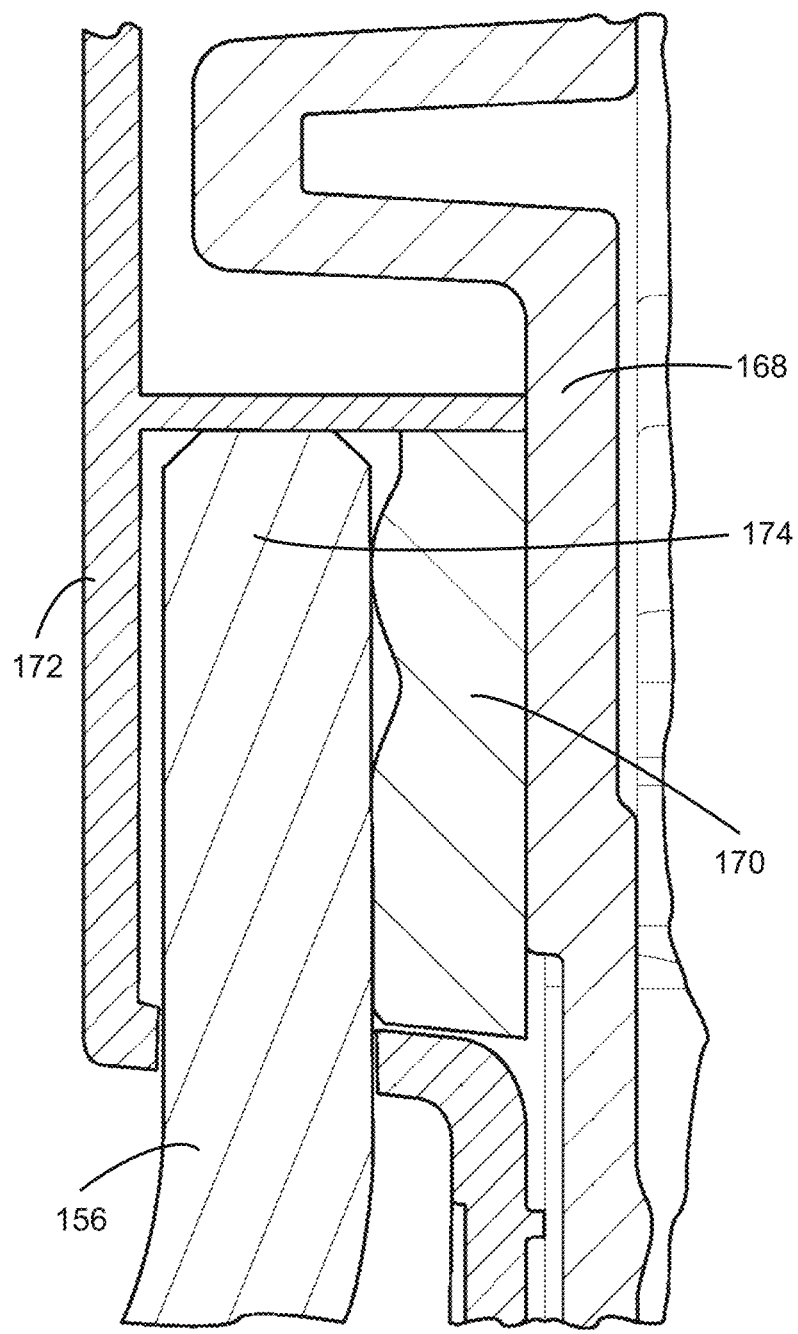
FIG. 5 illustrates an embodiment of a clamp for connecting a housing and a stand of a sleep monitoring device.

The stand clamp 170 rests against the back surface 172 of the housing 150 and captures the ends 174 of the stand 156 in a press-fit as shown in FIG. 5 to resist removal of the stand 156 after assembly. The stand clamp 170 is formed of a deformable material, such as a deformable plastic, rubber, or other such material capable of deforming in response to an applied force. In some embodiments, the stand 156 may be connected through the press-fit as a result of the stand clamp 170 and back surface 172 forming an opening to receive ends 174, the opening having a diameter smaller than a diameter of the ends 174. The stand clamp 170 may be held against the back surface 172 by pressure from the heat sink 168 or other components within the housing 150. In this manner, the heat sink 168 and back surface 172 compress the stand clamp 170 and hold it in place to receive the ends 174. The sleep monitoring device 110 may be shipped disassembled, with the stand 156 disconnected from the housing 150. As shown, the housing 150, formed of the front surface 152, perimeter 178, and back surface 172, is assembled with integral fasteners, such as clips, recesses, detents, and the like, rather than with fasteners such as threaded connectors. Upon receiving the sleep monitoring device 110, the user may assemble the stand 156 and housing 150 by inserting the ends 174 into openings in the housing 150 to engage with the stand clamp 170 without the use of hand tools to tighten or assemble any connectors. The stand 156 may likewise be removed by overcoming the friction of the press-fit of the stand clamp 170 against the ends 174.

FIG. 4 illustrates an embodiment of an installation of a millimeter wave radar chip in the housing of the sleep monitoring device. The sleep monitoring device 110 may be the sleep monitoring device 110 of FIGS. 1-3 and include the components described and associated therewith including the front surface 152, perimeter 178, back surface 172, heat sink 168, processor board 166, millimeter wave radar chip 160, input mechanism 158, stand 156, and other such elements described in association therewith. In FIG. 4, the sleep monitoring device 110 is shown in a section view, with the section taken parallel to the front surface 152 such that the interior of the housing 150 is visible as though the front surface 152 were removed.

As depicted in FIG. 4, the millimeter wave radar chip 160 is oriented at a non-zero angle relative to the axis 180, which is a vertical axis of the sleep monitoring device 110. The millimeter wave radar chip 160 is oriented at an angle of between thirty and sixty degrees, such as an angle of forty-five degrees. The non-zero angle relative to the vertical axis enables the antenna array to receive RF signals and reduces the impact of signal strength fluctuations due to polarization angle differences and multi-path cancellation of RF signals.

In some embodiments, the millimeter wave radar chip 160 may be oriented parallel to, or aligned with the axis 180 while the antenna array 162 is oriented at a non-zero angle, such as between thirty and sixty degrees, or at or about forty-five degrees relative to the axis 180. The antenna array 162 may be oriented on the millimeter wave radar chip 160 at an angle such that the millimeter wave radar chip 160 may have an edge parallel and/or perpendicular to the axis 180 while maintaining the antenna array at the angle described above relative to the axis 180.

FIG. 5 illustrates an embodiment of a clamp for connecting a housing and a stand of a sleep monitoring device. The clamp is the stand clamp 170 of FIG. 3 and is shown held in place between the back surface 172 and the heat sink 168. The stand clamp 170 is formed of a deformable material, such as a deformable plastic, rubber, or other such material capable of deforming in response to an applied force. The stand clamp 170 may, for example be a rubber having a Shore A durometer in a range of twenty to seventy. The stand clamp 170 receives the ends 174 as they are inserted through the back surface 172 and the stand clamp deforms in response to the press-fit of the ends 174 into the space formed between the stand clamp 170 and the back surface 172. The deformation of the stand clamp 170 results in resistance against removal of the stand 156 from the housing 150 after insertion, thereby enabling tool-less installation of the stand 156 and housing 150. The stand 156 may be removed from the housing 150 by overcoming the friction between the stand clamp 170 and the stand 156, which may be accomplished without tools.

Figure 6:
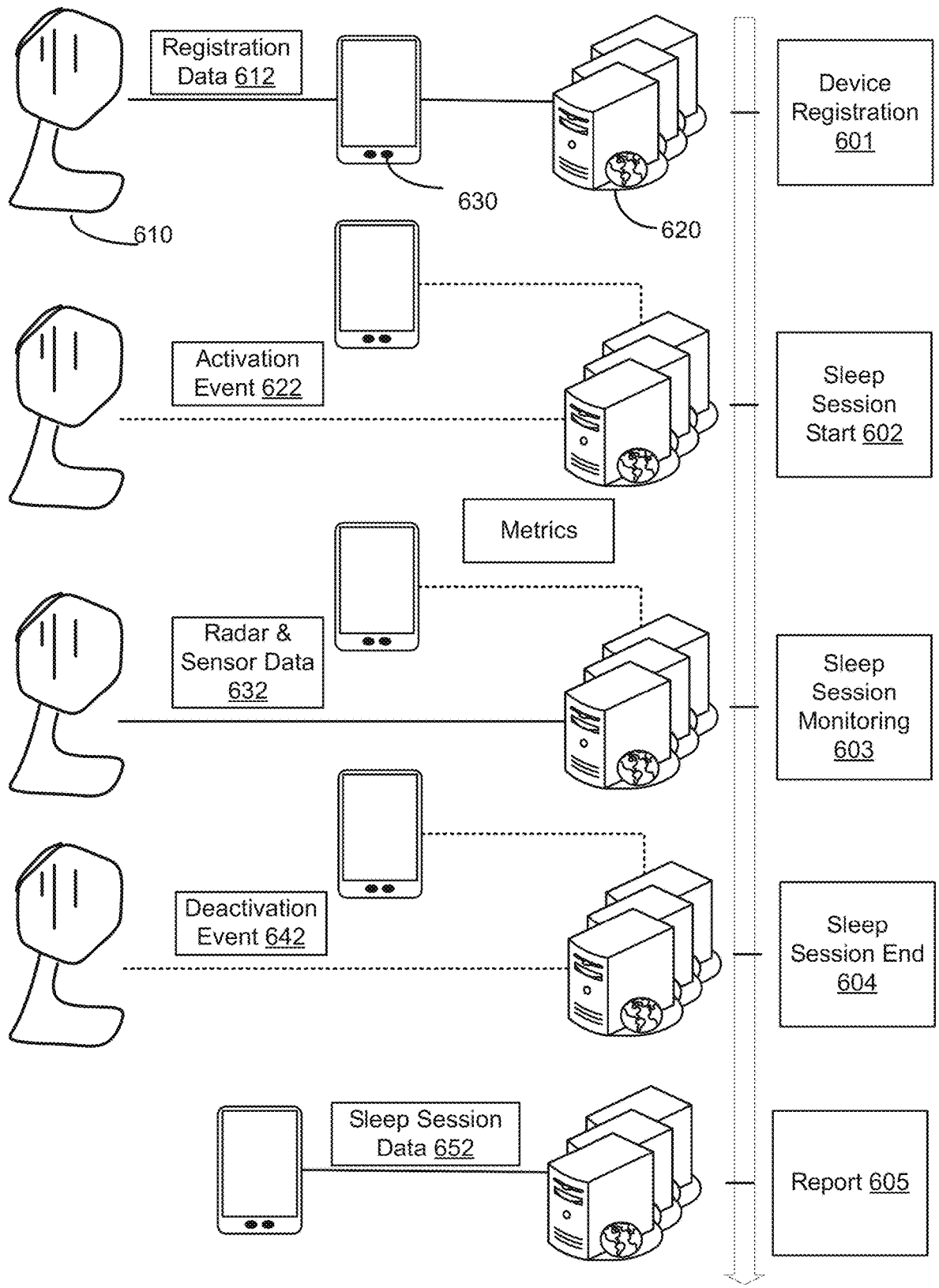
FIG. 6 illustrates an embodiment of stages for using a sleep monitoring system.

FIG. 6 illustrates an embodiment of stages for using a sleep monitoring system. These stages represent operational stages that may be performed, starting with registering a sleep monitoring device 610 with a computer system 620 of a service provider and ending with reporting sleep session data to a user device 630 that may be also registered with the computer system 620. The sleep monitoring device 610 is an embodiment of any of the sleep monitoring devices described herein above. the computer system 620 and the user device 630 are embodiments of the computer system 120 and the user device 130, respectively, of FIG. 1.

As illustrated, in a first stage, a device registration 601 is performed and can involve the sleep monitoring device 610, the computer system 620, and the user device 630. Generally, the device registration 601 results in registering the sleep monitoring device 610 under a user account managed by the computer system 620. The user device 630 may already be registered under that same user account and may facilitate the registration under the user account and the provisioning of the sleep monitoring device 610 to connect to a data network (e.g., to a home network or some other secure network via, for instance, WIFI or some other communication protocol). In an embodiment, user device 630 and the sleep monitoring device 610 establish a data connection using a communication protocol (e.g., BLUETOOTH) and exchange registration data 612, such as an identifier of the sleep monitoring device 110 (e.g., its media access control (MAC) address and/or product serial number), an encryption key of the sleep monitoring device 110, an identifier of the user account (e.g., username), and/or a credential (e.g., a user account password, a digital certificate, and the like). The user device 630 can send the registration data 612 to the computer system 620. Upon user authentication or device authentication, the device information (e.g., device identifier) of the sleep monitoring device 610 can be added to the user account. An identifier and a credential of the data network (e.g., a service set identifier (SSID) and a password) can be retrieved from the user account and/or provided directly from the user device 630 to the sleep monitoring device 610 such that the sleep monitoring device 610 can connect to the data network using the same or a different communication protocol (e.g., WIFI) to then communicate with the computer system 620 without the user device 630 being an intermediary of the communications.

In a second stage, a start 602 of a sleep session is detected. The start 602 triggers the sleep monitoring device 610 to activate its mmwave radar chip and start the stream of radar data and sensor data to the computer system 620. The start 602 can be detected based on an activation event 622. Different activation event types are possible and can involve one or more of the sleep monitoring device 610, the computer system 620, or the user device 630 (as indicated with the dotted lines). In one embodiment, the sleep monitoring device 610 includes an input mechanism. Upon an activation of this input mechanism (e.g., a button push), the activation event 622 is detected. In another embodiment, the computer system 620 stores an activation schedule under the user account. Upon a start indicated in this schedule, the computer system 620 sends instruction data to the sleep monitoring device 610, where the receipt of the instruction data corresponds to the activation event 622. In a further embodiment, the detection of the start 602 can be distributed between the sleep monitoring device 610 and the computer system 620. For instance, and continuing with the activation schedule example, the sleep monitoring device 610 sends radar data and sensor data upon the activation event 622. The computer system 620 determines, based on macro-level motion detection and/or micro-level motion detection, whether a target is present. If so, the computer system 620 starts the sleep session. In another embodiment, a sleep application on the user device 630 can receive, via a user interface, user input requesting the start 602. In this case, the user device 630 sends request data to the computer system 620 for the start 602 and, in turn, the computer system 620 sends the instruction data to the sleep monitoring device 610.

In a third stage, the sleep session has started and sleep session monitoring 603 is performed. For example, the sleep monitoring device 610 sends radar and sensor data 632 to the computer system 620. The computer system 620 may, but need not (as indicated with the dotted line), generate and send in real-time metrics about the sleep session to the user device 630.

In a fourth stage, an end 604 of the sleep session is detected. The end 604 triggers the sleep monitoring device 610 to deactivate its mmwave radar chip and stop streaming radar data and sensor data to the computer system 620. The end 604 can also trigger the computer system 620 to perform any incomplete data analysis to generate sleep session data. The end 604 can be detected based on a deactivation event 642. Different deactivation event types are possible and can involve one or more of the sleep monitoring device 610, the computer system 620, or the user device 630 (as indicated with the dotted lines). The deactivation event, such as the end 604 need not be of the same type as the activation event 622. In one embodiment, the input mechanism (or another button of the sleep monitoring device 610) is selected again and this selection results in the deactivation event 642. In another embodiment, upon an end indicated in the activation schedule stored under the user account, the computer system 620 sends instruction data to the sleep monitoring device 610, where the receipt of the instruction data corresponds to the deactivation event 642. In a further embodiment, the detection of the end 604 can be distributed between the sleep monitoring device 610 and the computer system 620. For instance, and continuing with the activation schedule example, the sleep monitoring device 610 sends radar data and sensor data. The computer system 620 determines whether a previously detected target is no longer present based on a macro-level motion detection and/or micro-level motion detection. target is present. If so, the computer system 620 ends the sleep session. In another embodiment, the sleep application on the user device 630 may also include a predefined sleep window defining a start and stop sleep session time, for example defining a typical time when a user goes to sleep and wakes up. In another embodiment, the sleep application on the user device 630 can also receive, via the user interface, user input requesting the end 604. In this case, the user device 630 sends request data to the computer system 620 for the start 602 and, in turn, the computer system 620 sends the instruction data to the sleep monitoring device 610.

In a fifth stage, the sleep session has ended and a report 605 can be generated about the sleep session. For example, the computer system 620 complete the processing and analysis of the received radar and sensor data 632 sent during the sleep session. The resulting sleep session data 652 can be sent, using a push mechanism or a pull mechanism, to the user device 630. In addition, the sleep session data 652 can be stored in the user account.

Figure 7:
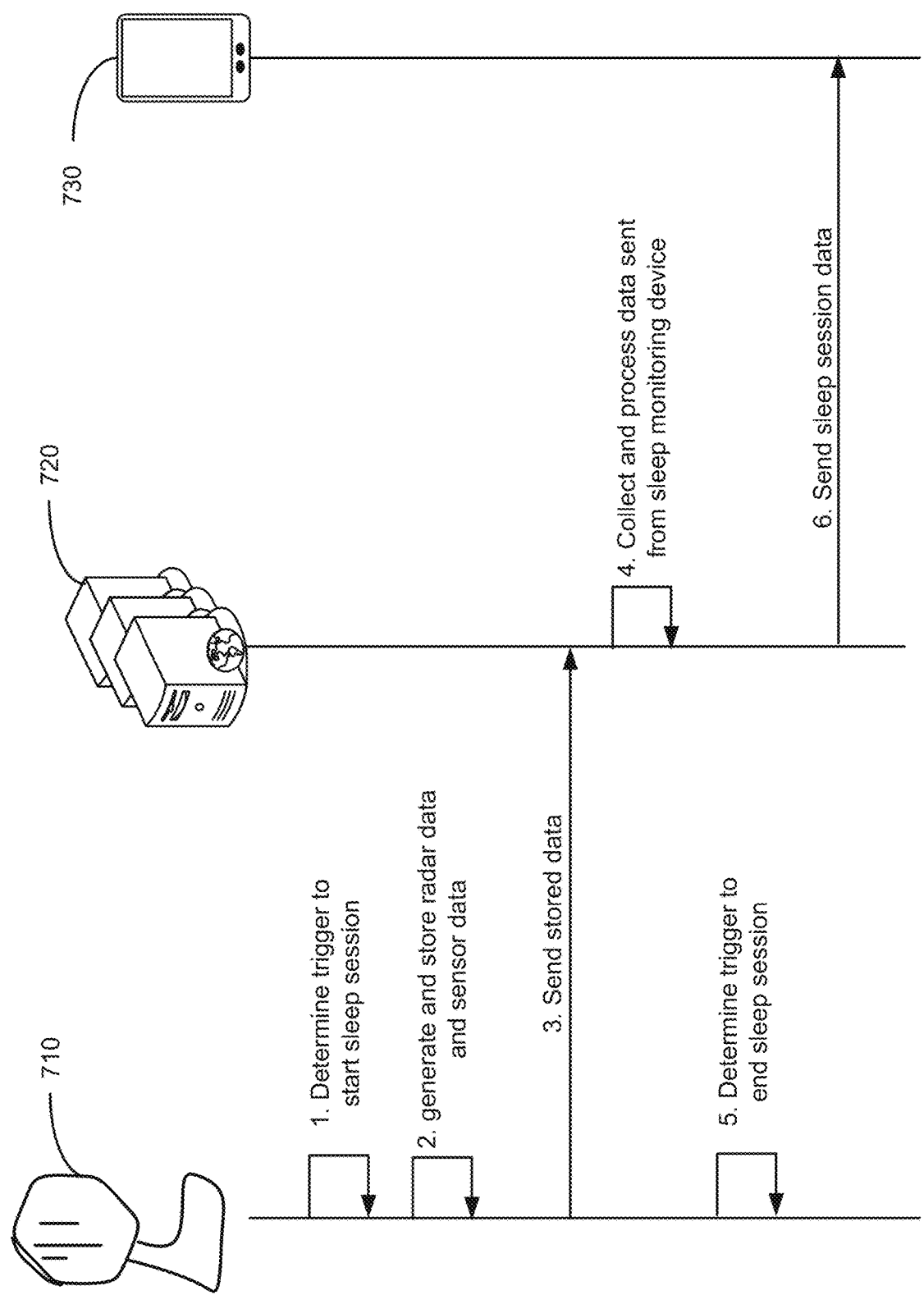
FIG. 7 illustrates an embodiment of a sequence diagram for sleep monitoring.

FIG. 7 illustrates an embodiment of a sequence diagram for sleep monitoring. The sleep monitoring can involve a sleep monitoring device 710, a computer system 720, and a user device 730 that are embodiments of the sleep monitoring device 610, the computer system 620, and the user device 630, respectively, of FIG. 6. The sleep monitoring can be performed during a sleep session and sleep session data can be reported at the end of the sleep session.

As illustrated, the sequence diagram includes a determination by the sleep monitoring device 710 of a trigger to start the sleep session. This trigger can be an activation event based on a local selection of an input mechanism of the sleep monitoring device 710, instruction data from the computer system 720, and/or request data from the user device 730. Next, the sleep monitoring device 710 generates and stores radar data and sensor data. For instance, the sleep monitoring device 710 activates a mmwave radar chip. mmwave RF signals are transmitted in pulses for a duration of ten milliseconds every one hundred milliseconds (or at different transmission rates). mmwave RF signals that are received back can be processed at a particular frame rate. The resulting radar data is stored in a buffer of the sleep monitoring device 710. Further, sensor data generated by sensors of the sleep monitoring device 710 are also stored in the buffer. The storage can be asynchronous, where the radar data and the sensor data are stored as binary files in a queue depending on their timing.

In a third step of the sequence diagram, the sleep monitoring device 710 sends the stored data (e.g., the radar data and the sensor data) to the computer system 720. For instance, the data storage and transmission can be repeated at a particular interval rate, such that binary files can be streamed to the computer system 720 at the interval rate (e.g., every five minutes for radar data and every thirty minutes for sensor data and other data).

Over time, the computer system 720 collects and processes data that was sent from the sleep monitoring device 710 during the sleep session. The data collection can include storing the received radar data (e.g., the corresponding binary files) and the received sensor data (e.g., the corresponding binary files). The processing can include analysis of collected data including, for instance, data fusion, ML processing, pattern detection, statistical analysis, and the like. Parts of the analysis may be performed before an end of the sleep session and remaining parts may be performed thereafter.

At some point in time, the sleep monitoring device 710 determines a trigger to end the sleep session. This trigger can be deactivation event based on a local selection of an input mechanism (or another button) of the sleep monitoring device 710, instruction data from the computer system 720, and/or request data from the user device 730. In response to the trigger, the sleep monitoring device 710 deactivates the mmwave radar chip and stops the storing and sending of radar data and sensor data. Upon detection of the trigger event, depending on an activation schedule, upon no longer receiving data from the sleep monitoring device 710, and/or upon an interrogation of the sleep monitoring device 710, the computer system 720 generates sleep session data from the collected data. The sleep session data, or at least a portion thereof, can be sent to the user device 730.

Figure 8:
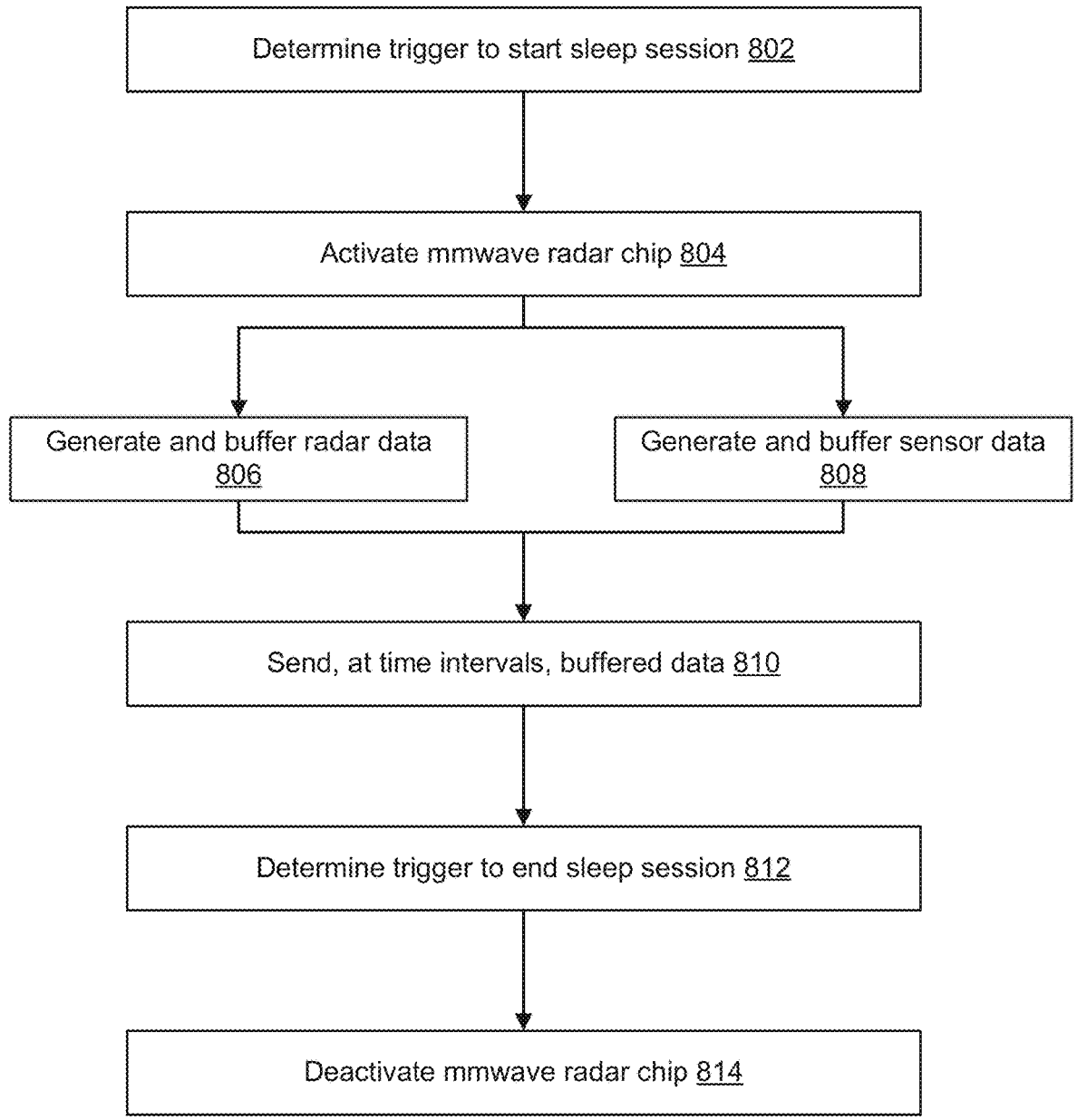
FIG. 8 illustrates an embodiment of a flow for generating radar and sensor data by a sleep monitoring device.

FIG. 8 illustrates an embodiment of a flow for generating radar and sensor data by a sleep monitoring device. Operations of the flow can be performed by a sleep monitoring device, such as the sleep monitoring device 710 of FIG. 7.

Some or all of the instructions for performing the operations can be implemented as hardware circuitry and/or stored as computer-readable instructions on a non-transitory computer-readable medium of the sleep monitoring device. As implemented, the instructions represent modules that include circuitry or code executable by processor(s) of the sleep monitoring device. The use of such instructions configures the sleep monitoring device to perform the specific operations described herein. Each circuitry or code in combination with the relevant processor(s) represent a means for performing a respective operation(s). While the operations are illustrated in a particular order, it should be understood that no particular order is necessary and that one or more operations may be omitted, skipped, performed in parallel, and/or reordered.

In an embodiment, the flow can start at operation 802, where the sleep monitoring device determines a trigger to start a sleep session. At operation 804, the sleep monitoring device activates a mmwave radar chip based on the trigger. For instance, the mmwave radar chip is powered up and/or instruction data is provided thereto by one or more processors, such as the processing chip of the sleep monitoring device to start mmwave RF signal transmission and reception.

At operation 806, the sleep monitoring device generates and buffers radar data. For instance, mmwave RF signal transmissions are performed at a transmission rate. Reflected mmwave RF signals are received and processed at a particular data rate and can have a particular data resolution. The processing results in the radar data and the radar data can be stored as a binary file in the buffer.

At operation 808, the sleep monitoring device generates and buffers sensor data. For instance, the sleep monitoring device can include multiple sensors that sense different types of environmental data, such as temperature, humidity, and ambient light. Each sensor can generate sensor data at a particular data rate and a particular data resolution. The data rate and/or data resolution need not be the same across the sensors and/or the mmwave radar chip. The sensor data of each sensor can be stored a binary file in the buffer.

At operation 810, the sleep monitoring device sends, at time intervals, buffered data. The buffered data can include binary files of the radar data and sensor data that have been queued in the buffer.

At operation 812, the sleep monitoring device determines a trigger to end the sleep session. At operation 814, the sleep monitoring device deactivates the mmwave radar chip based on the trigger. For instance, the mmwave radar chip is powered up and/or instruction data is provided thereto by the one or more processors embodied within the sleep monitoring device to stop mmwave RF signal transmission and reception.

Although no illustrated in the flow of FIG. 8, additional operations can be implemented and can relate to the detection of a target. In particular, the radar data can include a point cloud (e.g., a two-dimensional (2D) point cloud) indicating a distance to the target. The radar data can additionally or alternatively include macro-level motion data (e.g. motion of a target's body, rather than chest displacement) and/or target presence detection confidence data (e.g., a percentage indicating the confidence in the detection of the target by the mmwave radar chip). Referring to the point cloud, a target can be identified therefrom and can be associated with micro-level respiration data (e.g., respiratory rate given the chest displacement over time). The target can be tracked over time. If at some point, the target is no longer identified for a certain period of time, the one or more processors can determine that the target is no longer present. In this case, the processing device can stop storing and/or sending radar and sensor data to the computer system and/or can determine the trigger to end the sleep session. Similarly, and referring to the macro-level motion data and/or the presence detection confidence data, if the one or more processors can determine that the target is no longer present given one or both types of data, the processing device can stop storing and/or sending radar and sensor data to the computer system and/or can determine the trigger to end the sleep session.

Figure 9:
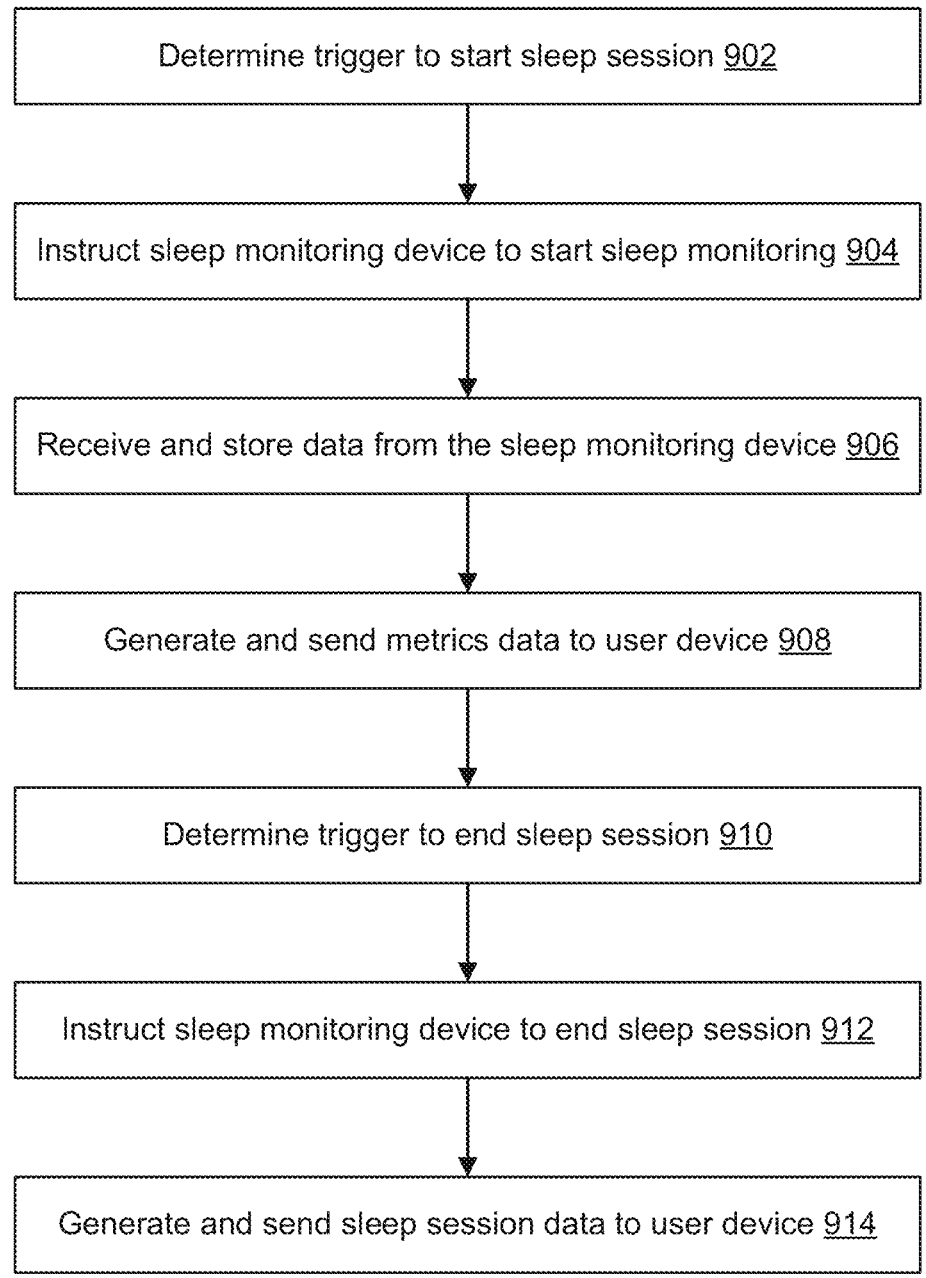
FIG. 9 illustrates an embodiment of a flow for generating sleep monitoring data by a computer system.

FIG. 9 illustrates an embodiment of a flow for generating sleep monitoring data by a computer system. Operations of the flow can be performed by a computer system, such as the computer system 720 of FIG. 7. Some or all of the instructions for performing the operations can be implemented as hardware circuitry and/or stored as computer-readable instructions on a non-transitory computer-readable medium of the computer system. As implemented, the instructions represent modules that include circuitry or code executable by processor(s) of the computer system. The use of such instructions configures the computer system to perform the specific operations described herein. Each circuitry or code in combination with the relevant processor(s) represent a means for performing a respective operation(s). While the operations are illustrated in a particular order, it should be understood that no particular order is necessary and that one or more operations may be omitted, skipped, performed in parallel, and/or reordered.

In an embodiment, the flow can start at operation 902, where the computer system determines a trigger to start a sleep session. In an embodiment, the trigger is an activation event based on an activation schedule stored in a user account associated with a sleep monitoring device. In another embodiment, the trigger corresponds to a request data received from a user device to start the sleep session, where the user device is also associated with the user account. In yet another embodiment, the sleep monitoring device can send instruction data to the computer system to start the sleep session, where this instruction data is sent upon a selection of an input mechanism of the sleep monitoring device.

At operation 904, the computer system instructs the sleep monitoring device to start sleep monitoring. For instance, the computer system sends instruction data to the sleep monitoring device to activate a mmwave RF chip and start streaming radar data and sensor data. In the case of the trigger originating from the sleep monitoring device, operation 904 may be skipped.

At operation 906, the computer system receives and stores data from the sleep monitoring device. For instance, the data is received as binary files that correspond to buffered radar data and buffered sensor data.

At operation 908, the computer system generates and sends metrics data to the user device. For example, particular application modules for processing the received data are invoked to generate metrics (e.g., average respiration rate and the like) in real-time. The metrics can be sent as the metrics data to the user device for presentation thereat. In some embodiments, the metrics may be presented at the completion of a sleep session and are not presented during the sleep session.

At operation 910, the computer system determines a trigger to end the sleep session. In an embodiment, the trigger is a deactivation event based on the activation schedule or based on a request data received from the user device. In another embodiment, the sleep monitoring device can send instruction data to the computer system to end the sleep session, where this instruction data is sent upon a re-selection of the input mechanism or a selection of a deactivation button of the sleep monitoring device.

At operation 912, the computer system instructs the sleep monitoring device to end the sleep monitoring. For instance, the computer system sends instruction data to the sleep monitoring device to deactivate a mmwave RF chip and stop streaming radar data and sensor data. In the case of the trigger originating from the sleep monitoring device, operation 912 may be skipped.

At operation 914, the computer system generates and sends sleep session data to the user device. For example, upon the end of the sleep session data, particular application modules for processing the data collected during the sleep session are invoked to generate the sleep session data (e.g., sleep stages, metrics of each sleep stage, and the like). The sleep session data can be sent to the user device based on a push mechanism or a pull mechanism.

Although no illustrated in the flow of FIG. 9, additional operations can be implemented and can relate to the detection of a target. In particular, and like the presence detection described herein above, the computer system can detect the presence of the target from the radar data (e.g., 2D point cloud, macro-level motion data, and/or presence detection confidence data). If at some point, the target is no longer identified for a certain period of time, the computer system can determine that the target is no longer present and, as a result, can determine the end of the sleep session and/or instruct the sleep monitoring device to stop the sleep monitoring. In some embodiments, the end of the sleep session may be determined by a predefined sleep window describing typical or user-defines start and end times. Upon reaching the end of the predefined sleep window, the computer system may cause the sleep monitoring device to stop gathering data, or to end the sleep session. In some embodiments, upon reaching the end of the predefined sleep window, the sleep monitoring device will, based on user preferences, determine whether to end the sleep session or to continue. For example, user preferences may result in the sleep monitoring device continuing to gather data after the end of the sleep window if a target is still detected in the environment.

Additionally, the radar data can be used to detect multiple targets. For example, upon the micro-level motion data (e.g., respiratory data) is tracked a first target, where the target's presence is determined and tracked based on the 2D point cloud, macro-level motion data, and/or presence detection confidence data. Upon this presence being no longer detected, the analysis subsequent radar data continues to determine whether a second target can be detected. If so, the micro-level motion data from the subsequent radar data can be attributed to the second target. Otherwise, no target presence is detected and the sleep session can be terminated.

Figure 10:
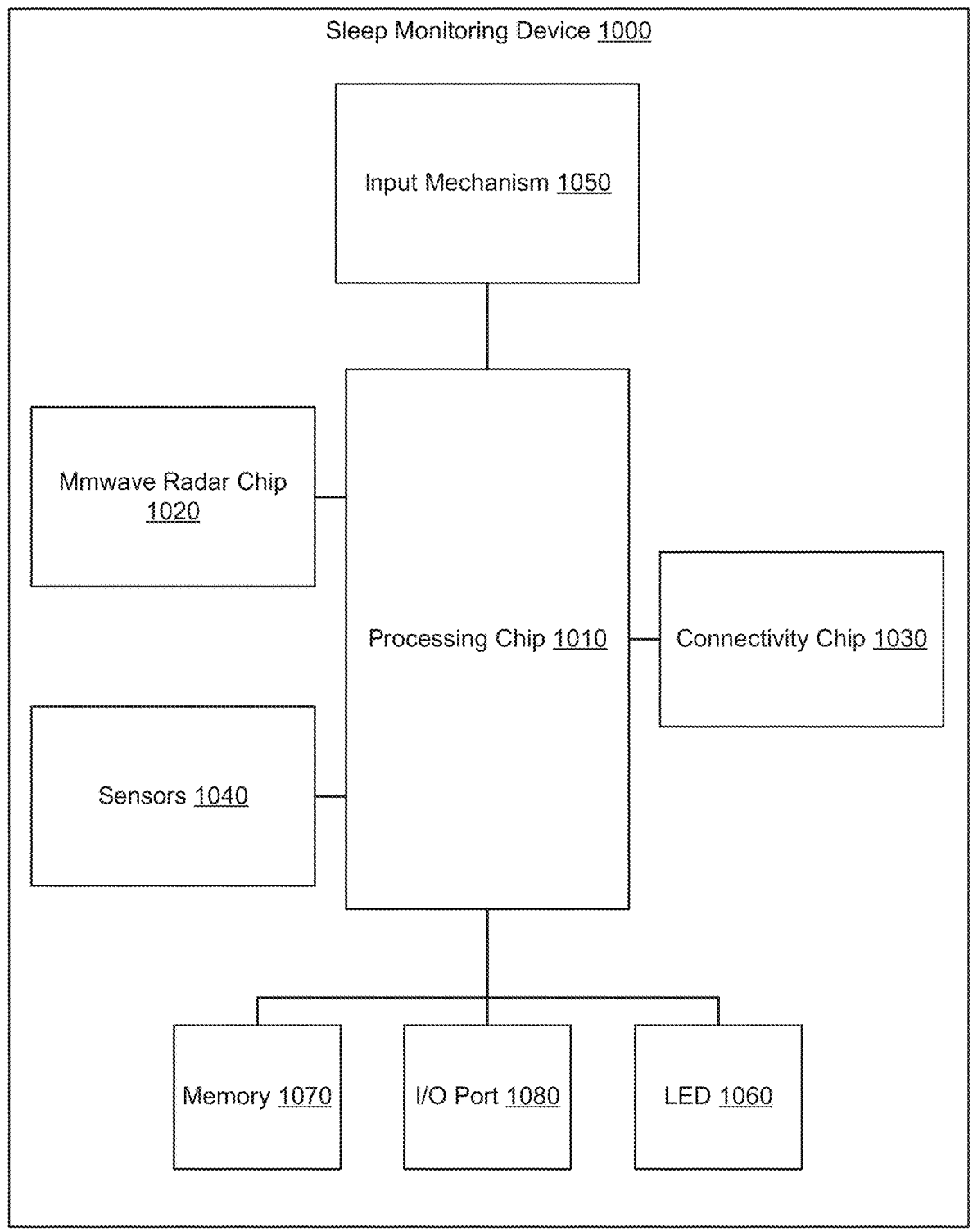
FIG. 10 illustrates an embodiment of computing components of a sleep monitoring device.

FIG. 10 illustrates an embodiment of computing components of a sleep monitoring device 1000. The sleep monitoring device 1000 is an embodiment of the sleep monitoring device 710 of FIG. 7. The computing components can include, for instance, a processing chip 1010 including one or more processors (which may be embodied in one or more chips or devices), a mmwave radar chip 1020, a connectivity chip 1030, sensors 1040, an input mechanism 1050, a light source 1060 (e.g., a set of light emitting diodes (LEDs), a memory 1070, and a set of input/output (I/O) ports 1080, among other components. The processing chip 1010 is communicatively coupled, via different interfaces, with the mmwave radar chip 1020, the connectivity chip 1030, sensors 1040, the input mechanism 1050, the light source 1060, the memory 1070, and the set of input/output (I/O) ports 1080 for controls thereto or therefrom.

In an embodiment, the processing chip 1010 includes one or more processors, one or more memories, one or more signal ports (e.g., for clocks), and one or more data ports mounted to a substrate (e.g., a printed circuit board (PCB)). For instance, the interface with the mmwave radar chip 1020 can include a serial peripheral interface (SPI) and/or general purpose I/O (GPIO) bus. The interface with the connectivity chip can include a secure digital I/O (SDIO) bus and/or a universal asynchronous receiver-transmitter (UART) bus. The interface with the sensor 1040 can include an inter-integrated circuit (I2C) bus. The interface with input mechanism 1050 can include I/O ports. In the illustrated case where the input mechanism 1050 includes a button, an I/O port can be set to a certain value (e.g., high) upon the activation of the input mechanism 1050 and to another value (e.g., low) otherwise. The interface with the light source 1060, the memory 1070, and the set of I/O ports 1080 can include pulse-width modulation (PWM) interface. In an illustrative embodiment, the processing chip 1010 can be implemented as a microcontroller, such as an RT600 MCU available from NXP SEMICONDUCTORS, Austin, Texas, U.S.A., programmed to perform the functionalities described in the present disclosure.

The mmwave radar chip 1020 includes one or more processors, one or more memories, one or more signal ports (e.g., for clocks), one or more RF input ports, one or more RF output ports, one or more RF filters, one or RF baseband processors, and one or more data ports mounted to a substrate (e.g., a PCB). On the substrate, a set of antenna arrays can be mounted. The set includes transmit antennas connected to the RF output ports, and receive antennas connected to the RF input ports. The mmwave radar chip 102 can be configured to transmit mmwave RF signals within a mmwave RF range (e.g., 50 GHz to 70 GHz) at a particular transmission rate. The mmwave radar chip 102 can be also configured to receive mmwave RF signals within the mmwave RF range (e.g., 50 GHz to 70 GHz) at a particular reception rate. Radar data can be generated at a particular data rate and data resolution based on the phase, amplitude, and/or frequency of the received mmwave RF signals and/or on change relative to the phase, amplitude, and/or frequency of the transmitted mmwave RF signals. In an illustrative embodiment, the mmwave radar chip 1020 can be implemented as a VYYR7201 chip available from VAYYAR IMAGING LMTD, Israel, programmed to perform the functionalities described in the present disclosure.

The radar data generated by the mmwave radar chip can indicate macro-level motion detection and micro-level motion detection. Macro-level motion detection generally relates to the motion of a target. In comparison, micro-level motion detection is more granular and can be specific to a particular portion of the target. For instance, the micro-level motion detection can relate to the displacement of the chest of the target, where the rate of chest displacement can be converted into a respiratory rate. In an embodiment, the radar data includes timestamps, a respiration per minute (RPM) metric, a range to the target (e.g., average distance to the target), an activity level (e.g., which can indicate the presence of the target), a breathing waveform, X, Y, and Z distances of the target from the mmwave radar chip 1020, identifies of voxels used for the data processing from a 2D point cloud, and a flag indicating whether upward pulse in the breathing waveform corresponds to an inhale or exhale.

The connectivity chip 1030 includes one or more processors, one or more memories, one or more signal ports (e.g., for clocks), one or more RF input ports, one or more RF output ports, one or more RF filters, one or RF baseband processors, and one or more data ports mounted to a substrate (e.g., a PCB). Multiple communications protocols can be supported including, for instance, BLUETOOTH and WIFI. BLUETOOTH can be used to pair the sleep monitoring device 1000 with a user device during, for instance, a registration and provisioning process. WIFI can be used to connect to a data network for communication with a computer system. In an illustrative embodiment, the connectivity chip 1030 can be implemented as a BCM43013 chip available from BROADCOM, San Jose, CA, U.S.A., programmed to perform the functionalities described in the present disclosure.

The sensors 1040 can sense data about an environment where the sleep monitoring device 1000 may be operated. For example, the sensors 1040 include a temperature sensor that senses the temperature of the environment, a humidity sensor that senses the humidity of the environment, and an ambient light sensor that senses the ambient light of the environment. The sensors 1040 can also sense data about the sleep monitoring device 1000 itself. For instance, the sensors 1040 include a six-axis accelerometer gyroscope and a magnetometer usable to detect a change to the sleep monitoring device 1000's position. Further, the sensors 1040 include one or more temperature sensors installed within the housing of the sleep monitoring device 1000 to sense the operational temperature of the sleep monitoring device 1000 or of components thereof (e.g., of the mmwave radar chip 1020).

In an embodiment, the input mechanism 1050 may be a button, which can be operated to indicate beginning/ending of a sleep session. Of course other implementations of the input mechanism 1050 are possible, such as toggle button, capacitive touch, or a slide button. As described herein above, the input mechanism 1050 can be mounted within the same housing as the ambient light sensor. In another embodiment, the input mechanism 1050 can include additional or alternative devices that support different types of input and output modalities. For instance, the input mechanism 1050 can support a voice-based interface, where a natural language utterance of a user can be converted into a command to start and/or end a sleep session. In this embodiment, the voice-based interface can be provided by an audio processing front end. This audio processing front end includes wakeword engine that detects a wakeword and sends audio data of the natural language utterance to a backend system (e.g., the computer system 130) for processing (where this processing includes automatic speech recognition (ASR) and natural language understanding (NLU)). A command may be received back and provides from the audio processing front end to the processing chip. Additionally or alternatively, some of the ASR and/or NLU processing can be handled by the audio processing front end. In another embodiment, the input mechanism 1050 can support a gesture-based interface. In this case, the gesture-based interface can be provided by an optical front end that includes optical sensors and processors to detect and convert a gesture into a command related to the start and/or end of a sleep session. Other types of input mechanism 1050 are also possible, such as a proximity sensor, a motion sensor, a capacitive touch sensor, and the like.

Input mechanism 1050 need not be limited to a physical button. In other embodiments, input mechanism 1050 may be a microphone. In this embodiment, a user can issue an audible command to the sleep monitoring device to start or end a sleep monitoring session. The microphone then receives the audio command. The sleep monitoring device may additionally include audio front end circuitry (AFE) that receives the audio/audible command, generates associated audio data and performs speech processing on the audio data to determine a user intent associated with the audible command. In one instance, the sleep monitoring device may perform automatic speech recognition (ASR) to detect a wake word (e.g., "Alexa") and also perform natural language understanding (NLU) processing on the received audio to determine an action associated with the audible command. In another embodiment, the sleep monitoring device may perform wake word detection but send the audio data to a remote system for NLU (and other) processing. The remote system may then send data back to the sleep monitoring system indicating an action to the performed. The sleep monitoring device can then perform that action (e.g., start or end a sleep monitoring session). In yet another embodiment, input mechanism 1050 could also be a touch screen and the user may interact with GUI controls displayed on the touch screen to operate the device. One skilled in the art will realize that many other forms of input devices/mechanism can be implemented to accomplish the intended operations.

The light source 1060 can be controlled to indicate to the target that sleep monitoring is activated. In some embodiments, a light property (color, brightness, pattern, etc.) is controllably used for this indication. The t light property can also be controlled based on the detected ambient light. The use of the ambient light detection may not be limited to the light property control. Instead, the ambient light sensor data can be part of the sensor data sent to a computer system for the sleep monitoring analysis and creation of the sleep session data.

The memory 1070 can be an electronic non-volatile computer memory storage medium that can be electrically erased and reprogrammed, such as a flash memory. Program code for execution by the processing chip 1010 can be stored in the memory 1070. In addition, the memory 1070 can include a buffer that queues the radar data and sensor data that are to be sent by the processing device 1010 to the computer system via the connectivity chip 1030.

The I/O port 1080 can be used to troubleshoot the sleep monitoring device 1000. For instance, the I/O port is wired port, such as a universal serial bus (USB) port, that can be connected with a troubleshooting device.

Although not illustrated in FIG. 10, the sleep monitoring device 1000 can include a power source (e.g., a rechargeable battery) or an interface to an external power source (e.g., an alternating current (AC) adapter), and power circuitry (e.g., direct current (DC)-to-DC converters) to supply power at different level to the different computing components. The power supply can be limited to a maximum limit. In certain situations, mmwave RF transmissions may coincide with the data transmissions (e.g., via WIFI) and can correspond to aligned power peaks. The maximum limit can be set to be larger than the sum of these power peaks. Additionally or alternatively, power management can be implemented. For instance, the power circuitry can include capacitor circuit that stores and supplies energy to the connectivity chip 1030, mmwave radar chip 1020, and/or the processing chip 1010 during the time when the peaks are aligned. The capacitor circuit can include a set of capacitors and buck/boost converted and can be placed in series between the power source and the connectivity chip 1030, mmwave radar chip 1020, and/or the processing chip 1010. In another embodiment, timing of the data transmissions can be controlled. For instance, the connectivity chip 1030 may not send data while the mmwave radar chip 1020 is transmitting mmwave RF signals. An I/O line may exist between the mmwave radar chip 1020 and the connectivity chip 1030. During a mmwave RF transmission, a particular value (e.g., a high) is set on the I/O line. Based on this value, the connectivity chip 1030 can determine that a current data transmission is prohibited. In yet another embodiment, the transmit power of the connectivity chip 1020 can be limited to a certain level such that, when the two peaks align, their sum does not exceed the maximum limit.

Figure 11:
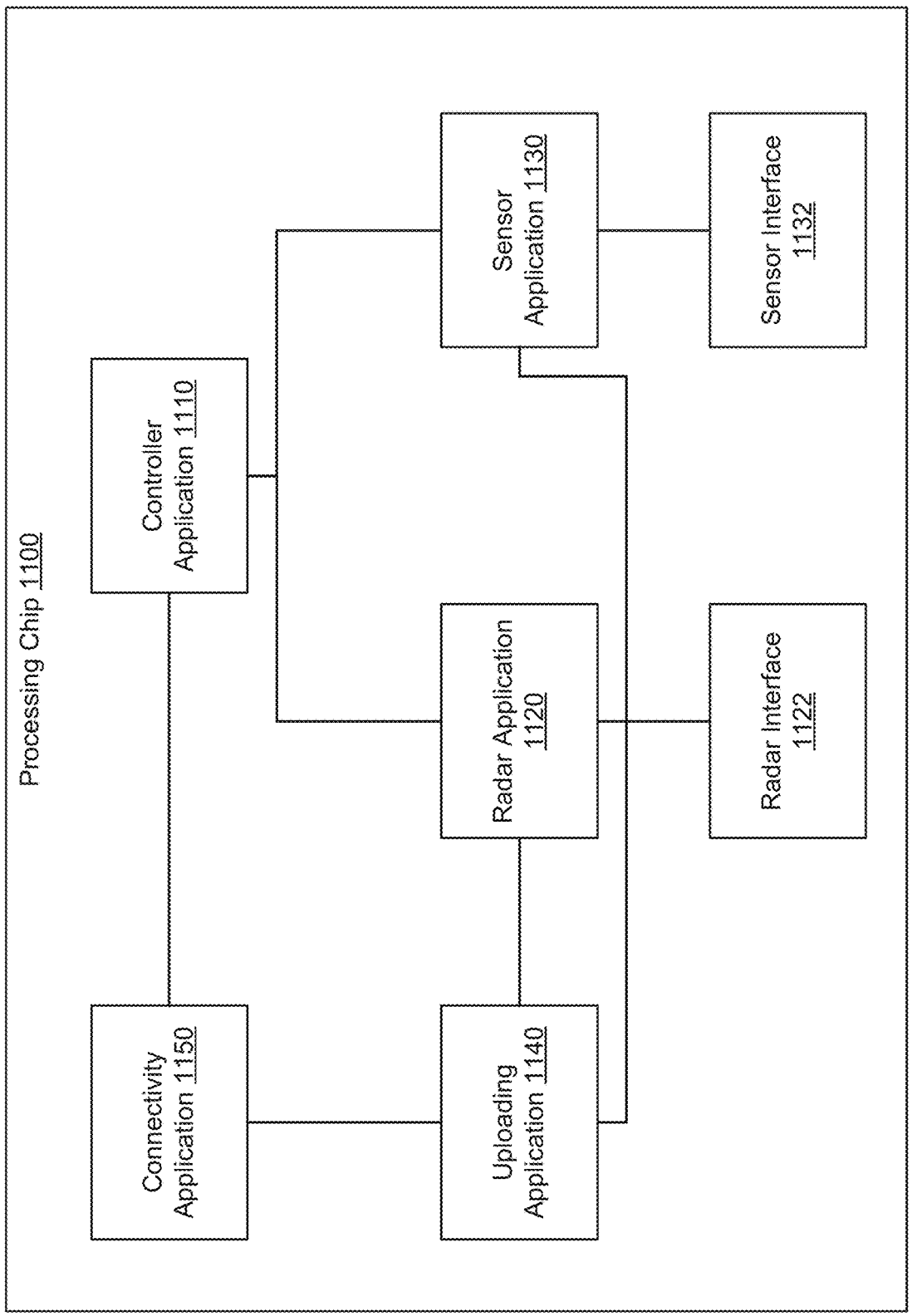
FIG. 11 illustrates an embodiment of application modules of a sleep monitoring device.

FIG. 11 illustrates an embodiment of application modules of a sleep monitoring device. The sleep monitoring device is an embodiment of the sleep monitoring device 1000 of FIG. 10. The application modules may be implemented as software modules on a processing chip 1100 (e.g., each as a set of computer-readable instructions or program code stored in one or more memories of the processing chip 1100 and executable by one or more processors of the processing chip 1100). The processing chip 1100 is an embodiment of the processing chip 1010 of FIG. 10. The application modules can include, for instance, a controller application 1110, a radar application 1120, a sensor application 1130, an uploading application 1140, and a connectivity application 1150.

In one embodiment, the controller application 1110 controls sleep monitoring functionalities of the sleep monitoring device by orchestrating the operations of at least the radar application 1120, the sensor application 1130, and the connectivity application 1150. For instance, the controller application 1110 sends instruction data to the radar application 1120 to activate/deactivate and/or start/end radar data collection of a mmwave radar chip of the sleep monitoring device, and instructions data to the sensor application 1130 activate/deactivate and/or start/end sensor data collection of a set of sensors of the sleep monitoring device. The controller application 1110 can also receive instruction data from the connectivity application 1150 about initiating a sleep session and/or ending a sleep session in response to a remote request for doing so (e.g., either from a computer system and/or a user device). Conversely, the controller application 1150 can inform the connectivity application 1150 about the start/end of the sleep session and/or collected radar/sensor data for reporting to the computer system and/or user device. As further described in the next figures, the controller application 1110 can maintain a state machine, where the current state indicated by the state machine can control aspects of the orchestration.

The radar application 1120 controls operations of the mmwave radar chip (e.g., the mmwave radar chip 1020 of FIG. 10). In some embodiments, a radar interface 1122, such as an application programming interface (API) exists between the radar application 1120 and the mmwave radar chip (or a radar application on such a chip). Instruction data can be sent from the radar 1120 application to activate/deactivate, start/end radar data collection, and/or maintain an operational state of the mmwave radar chip. Radar data can be received back via the radar API 1122, whereby the radar application 1120 can send the radar data to the uploading application 1140. As further described in the next figures, the radar application 1120 can maintain a state machine, where the current state indicated by the state machine can control the operational state of the mmwave radar chip.

The sensor application 1130 controls operations of the set of sensors (e.g., the sensors 1040 of FIG. 10). In some embodiments, a sensor interface 1132, such as an API, exists between the sensor application 1130 and the set of sensors (or a set of sensor applications of such sensor(s)). Instruction data can be sent from the sensor application 1130 to activate/ deactivate, start/end sensor data collection, and/or maintain an operational state of the sensor set. Sensor data can be received back via the sensor interface 1132, whereby the sensor application 1130 can send the sensor data to the uploading application 1140. Sensors of different types may exist. One API may be used per sensor or sensor type. The sensor application 1130 may collect, via such APIs, the different types of sensor data and may, but need not, aggregate such data before sending it to the uploading application 1140.

The uploading application 1140 receives the radar data from the radar application 1120 and the sensor data from the sensor application 1130. This received data can be stored in a buffer of memory of the processing chip 1100 or another memory (e.g., the memory 1070 of FIG. 10) by the uploading application 1140 or, alternatively, the radar data may be buffered by the radar application 1120 and the sensor data may be buffered by the sensor application 1130. The storage can be asynchronous, whereby data received at a particular time (e.g. radar data or sensor data) is stored as a first binary file at a position in a queue of the memory buffer, where the position is time dependent. At time intervals (e.g., periodically), the uploading application 1140 sends the buffered data (e.g., the binary files stored in the queue) to the connectivity application 1150 for data transmission to the computer system and/or user device. The uploading application 1140 may also support data re-transmission, whereby the buffered data can be resent to the connectivity application 1150 and is not removed from the memory buffer until after expiration of a retention time or an indication from the connectivity application 1150 of a successful data transmission.

The connectivity application 1150 provides connectivity functionality of the sleep monitoring device. For instance, the connectivity application 1150 supports a first communication protocol (e.g., BLUETOOTH) to connect the sleep monitoring device to the user device and complete a registration process. Further, the connectivity application supports a second communication protocol (e.g., WIFI) to connect the sleep monitoring device to the computer system and stream the data sent from the uploading application 1140 to the computer system. Request data received from the user device (e.g., as part of performing a registration process) or from the computer system (e.g., as a trigger to start/end a sleep session) can be translated into instruction data and sent to the controller application 1110. Although the connectivity application 1150 is illustrated in FIG. 11 as being an application module of the processing chip 1100, this connectivity application 1150 can be an application module of a connectivity chip (e.g., the connectivity chip 1030 of FIG. 10) and an interface therewith can be hosted on the processing chip 1100.

Accordingly and in an illustrative use case, the connectivity application 1150 receives request data from the user device about the registration. The connectivity application 1150 sends first instruction data to the controller application 1110 to return registration data. This registration data is sent back to the user device. Thereafter, the connectivity application 1150 receives request data from the computer system about a start of a sleep session. The connectivity application 1150 sends corresponding instruction data to the controller application 1110. Next, the controller application 1110 sends instructions data to the radar application 1120 to activate the mmwave radar chip and to the sensor application 1130 to activate the set of sensors. In turn, the radar application 1120 sends an API call via the radar interface 1122 to the mmwave radar chip about the activation and starts receiving radar data. This radar data is sent to the uploading application 1140. similarly, the sensor application 1130 starts receiving sensor data via the sensor interface 1132 and sends it to uploading application 1140. The radar application 1120, sensor application 130, or uploading application 1140 buffers the radar data and sensor data and, periodically, sends the buffered data to the connectivity application 1150. The connectivity application 1150 then sends the data received from the uploading application 1140 to the computer system.

Figure 12:
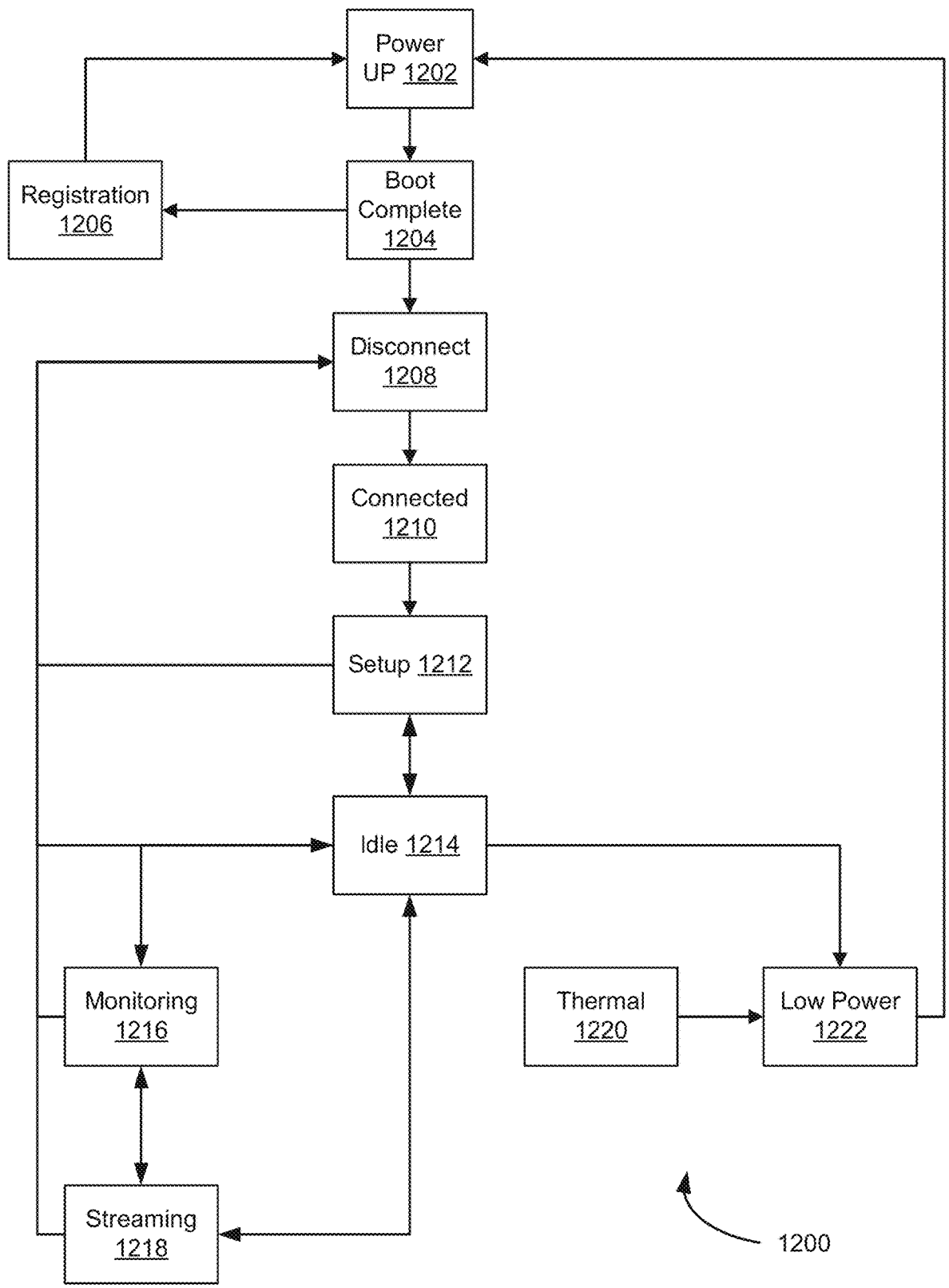
FIG. 12 illustrates an embodiment of a state machine of a sleep monitoring device.

FIG. 12 illustrates an embodiment of a state machine 1200 of a sleep monitoring device. The sleep monitoring device is an embodiment of the sleep monitoring device 1000 of FIG. 10. The state machine 1200 can be maintained by a controller application, such as the controller application 1110 of FIG. 11, and is usable to control sleep monitoring functionalities of the sleep monitoring device 1000.

As illustrated, when power is first supplied to the sleep monitoring device (e.g., from an external power source upon the sleep monitoring device being plugged into such a source, or from an internal power source upon a power switch activation), the state machine 1200 indicates a power up state 1202 of the sleep monitoring device. Next, a booting process is performed, the completion thereof is indicated as a boot complete state 1204 in the state machine 1200. A check is performed to determine whether the sleep monitoring device is registered with a user account. If not, a registration process is initiated and indicated with a registration state 1206 in the state machine 1200. Once the registration process is complete, the sleep monitoring device is restarted, as indicated with the loop between the registration state 1206 and the power up state 1202. Upon the sleep monitoring device being registered and following the booting, the state machine 1200 indicates a disconnect state 1208. The sleep monitoring device connects with a home network using a communication protocol (e.g., WIFI). Upon the connection, the state machine 1200 indicates a connected state 1210. Although not illustrated in FIG. 12, if the sleep monitoring device does not have the needed credentials to establish the connection (e.g., an SSID and password for an access point of the home network), the necessary connection data can be collected from one or more devices (e.g., from the user device during or after the registration process). Once connected, the state machine 1200 indicates a setup state 1212 of the sleep monitoring device.

The setup state 1212 can rely on position data from a set of sensors of the sleep monitoring device (e.g., inertial measurement unit (IMU) that includes an acceleration gyroscope and a magnetometer) to determine whether a calibration (following the connected state 1210) or a re-calibration (following an idle state 1214) is needed. The calibration can involve positioning the device at a particular positon (e.g., targeted angles relative to the X, Y, and Z axes) such as a target area is the field of view of a mmwave radar chip of the sleep monitoring device. For instance, guidance data can be provided from a computer system to a user device to instruct a user about positioning the sleep monitoring device. IMU data can be collected by the sleep monitoring device and sent to the computer system. The computer system can estimate the position (e.g., relative or absolute) of the mmwave radar chip and present associated information via the user device (e.g., can determine that estimated angles are outside of acceptable range of the targeted angles). The re-calibration can track a change to the previously calibrated position (e.g., a relative position change along the X, Y, and/or Z axes) and provide information, via the user device, for re-positioning the sleep monitoring device.

Once the setup is complete, the sleep monitoring device can enter the idle state 1210 of the state machine 1200. The setup state 1212 can be skipped and the idle state 1210 can immediately follow the connected state 1210 if, for instance, the sleep monitoring device reboots during a sleep session without instructions from the computer system (e.g., upon a system crash). Further, the setup state 1212 can follow the idle state 1214 for a re-calibration upon a detection of a change to the position of the sleep monitoring device (e.g., based on the IMU data). The disconnect state 1208 can also follow the idle state 1214 if the sleep monitoring device loses the data connection to the home network. If the sleep monitoring functionalities of the sleep monitoring device are not triggered for an extended period of time (e.g., for a period of time longer than predefined time period, such as one week or one month), a low power state 1222 follows the idle state 1214. In the low power state 1222, various functionalities of the sleep monitoring device, including transmit functionalities, receive functionalities, and/or processing functionalities, are deactivated to reduce the overall power consumption.

If none of the disconnect state 1208, setup state 1212, and lower power state 1222 are triggered while the sleep monitoring device is in the idle state 1214, the sleep monitoring functionalities can be triggered. Here, two sleep monitoring functionalities related states are possible and their use depends on the type of trigger. If the trigger is remote (e.g., instruction data from the computer system or request data from the user device), a monitoring state 1216 follows the idle state 1214. Likewise, upon a reboot (e.g., a system crash) that occurs during a sleep session, the monitoring state 1216 follows the idle state 1214. If the trigger is local (e.g., selection of an input mechanism of the sleep monitoring device), the monitoring state 1216 may be skipped and a streaming state 1218 immediately follows the idle state 1214. Transitions back from the monitoring state 1216 and stream state 1218 to the idle state 1214 and transitions therebetween and to the disconnect state 1208 are also possible.

In the monitoring state 1216, a sleep session has started and the mmwave radar chip is activated. Accordingly, presence of a target is monitored. If the presence is detected (e.g., presence detection confidence data indicates a high presence score for a predefined time period), the steaming state 1218 follows the monitoring state 1216. If the session stops or an error occurs, the idle state 1214 follows the monitoring state 1216. If connectivity is lost, the disconnect state 1208 follows the monitoring state 1216.

In the streaming state 1218, the sleep session has started, the mmwave radar chip is activated, and the presence is detected or a local trigger is activated. Accordingly, the sleep monitoring device sends radar data and sensor data to the computer system in a data stream. If the session stops or an error occurs, the idle state 1214 follows the streaming state 1218. If connectivity is lost, the disconnect state 1208 follows the streaming state 1218. If the presence is not detected or no longer detected (e.g., presence detection confidence data indicates a low presence score for a predefined time period), the monitoring state 1216 follows the streaming state 1218.

Further, the state machine 1200 include a thermal state 1220. In particular, the operational temperature of the sleep monitoring device is monitored over time. If the operational temperature exceeds an acceptable temperature range (e.g., due to a component failure, or excessive heat-up from the mmwave RF transmissions), a thermal event is declared and the thermal state 1220 is entered. if a sleep session was ongoing, the collection of radar data and sensor data is stopped in the thermal state 1220. The sleep monitoring device is then put in the low power state 1222. A reboot is performed and the power up state 1202 follows the low power state 1222.

Figure 13:
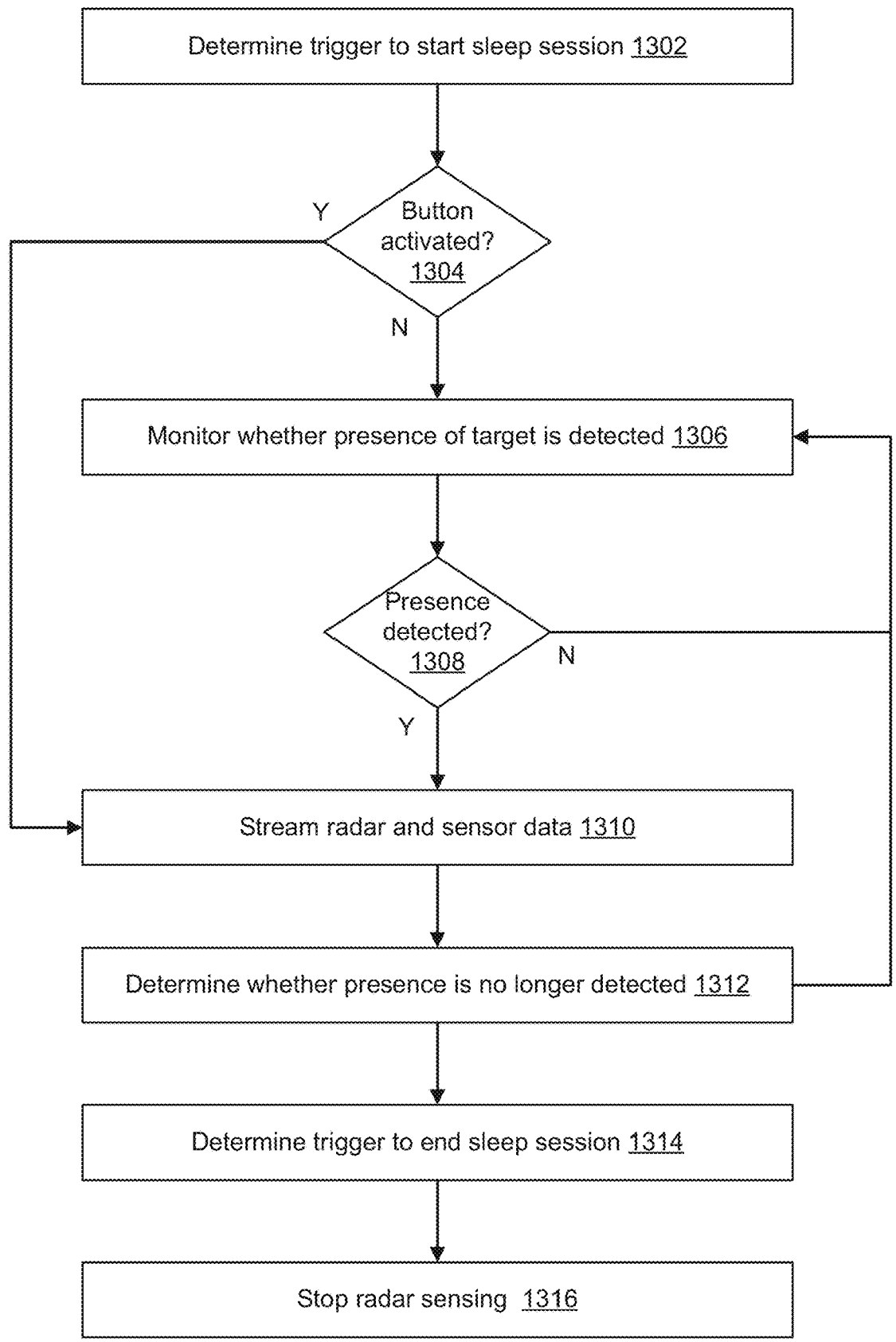
FIG. 13 illustrates an embodiment of a flow for controlling the streaming of radar and sensor data of a sleep monitoring device.

FIG. 13 illustrates an embodiment of a flow for controlling the streaming of radar and sensor data of a sleep monitoring device. Operations of the flow can be performed by a processing chip of a sleep monitoring device, such as the processing chip 1100 of FIG. 11, that implements an idle state, a monitoring state, and a streaming state within a state machine. Some or all of the instructions for performing the operations can be implemented as hardware circuitry and/or stored as computer-readable instructions on a non-transitory computer-readable medium of the sleep monitoring device (e.g., as a part of an application module, such as the controller application 1110 of FIG. 11). As implemented, the instructions represent modules that include circuitry or code executable by processor(s) of the sleep monitoring device. The use of such instructions configures the sleep monitoring device to perform the specific operations described herein. Each circuitry or code in combination with the relevant processor(s) represent a means for performing a respective operation(s). While the operations are illustrated in a particular order, it should be understood that no particular order is necessary and that one or more operations may be omitted, skipped, performed in parallel, and/or reordered.

As illustrated, the flow can start at operation 1302, where the sleep monitoring device determines a trigger to start a sleep session. The sleep monitoring device is in the idle state. The trigger can be a selection of an input mechanism of the sleep monitoring device and can be detected by the processing chip based on a data line with the input mechanism. Additionally or alternatively, the trigger can be remote from a computer system and a user device and can be detected as input to the processing chip from a connectivity chip of the sleep monitoring device.

At operation 1304, the sleep monitoring device determines whether the trigger is the selection of the button or not. This determination depends on the type of input to the processing chip (e.g., from the input mechanism or from the connectivity chip). If the selection is determined, operation 1310 follows operation 1304, where the streaming state is entered. Otherwise, operation 1306 follows operation 1304, where the monitoring state is entered.

At operation 1306, the sleep monitoring device monitors whether a presence of a target is detected. For example, a mmwave radar chip of the sleep monitoring device outputs radar data to the processing chip. The radar data includes presence detection confidence data indicating a score for the presence detected. This data can be collected by the processing chip over time.

At operation 1308, the sleep monitoring device determines whether the presence is detected. For example, if the score exceeds a predefined threshold score for a period of time longer than a predefined threshold duration, the processing chip determines that the presence is detected. In this case, operation 1310 follows operation 1308, whereby the streaming state is entered. Otherwise, operation 1308 loops back to operation 1306 to continue the presence monitoring, whereby the sleep monitoring device remains in the monitoring state.

At operation 1310, the sleep monitoring device steams radar and sensor data. For example, the processing chip receives radar data from the mmwave radar chip, and sensor data from a set of sensors of the sleep monitoring device. The received data is buffered and sent, at time intervals, to the computer system.

At operation 1312, the sleep monitoring device determines whether the presence is no longer detected. This operation can be similar to operation 1308. In particular, the processing chip continues the analysis of the presence detection confidence data. Here, however, the processing chip determines from that the score is lower than another, lower predefined threshold scope for a period of time that is also longer than the predefined threshold duration. In this case, operation 1312 loops back to operation 1306 to continue the presence monitoring, whereby the sleep monitoring device enters the monitoring state and need no longer send the collected radar and sensor data. If, however, the presence is detected, the streaming continues per operation 1310.

At operation 1312, the sleep monitoring device determines a trigger to end the sleep session. The trigger can be a selection of the input mechanism of and can be detected by the processing chip based on the data line with the input mechanism. Additionally or alternatively, the trigger can be remote from a computer system and a user device and can be detected as input to the processing chip from the connectivity chip of the sleep monitoring device.

At operation 1314, the sleep monitoring device stops render sensing and the data stream. For instance, the processing chip deactivates the radar chip by sending instructions thereto to stop the mmwave RF transmission and the creation of radar data. Further, the processing chip may, but need not, deactivate the set sensors. As such, no further radar data is collected and, optionally, no sensor data is collected. No data transmission via the connectivity chip is performed.

Figure 14:
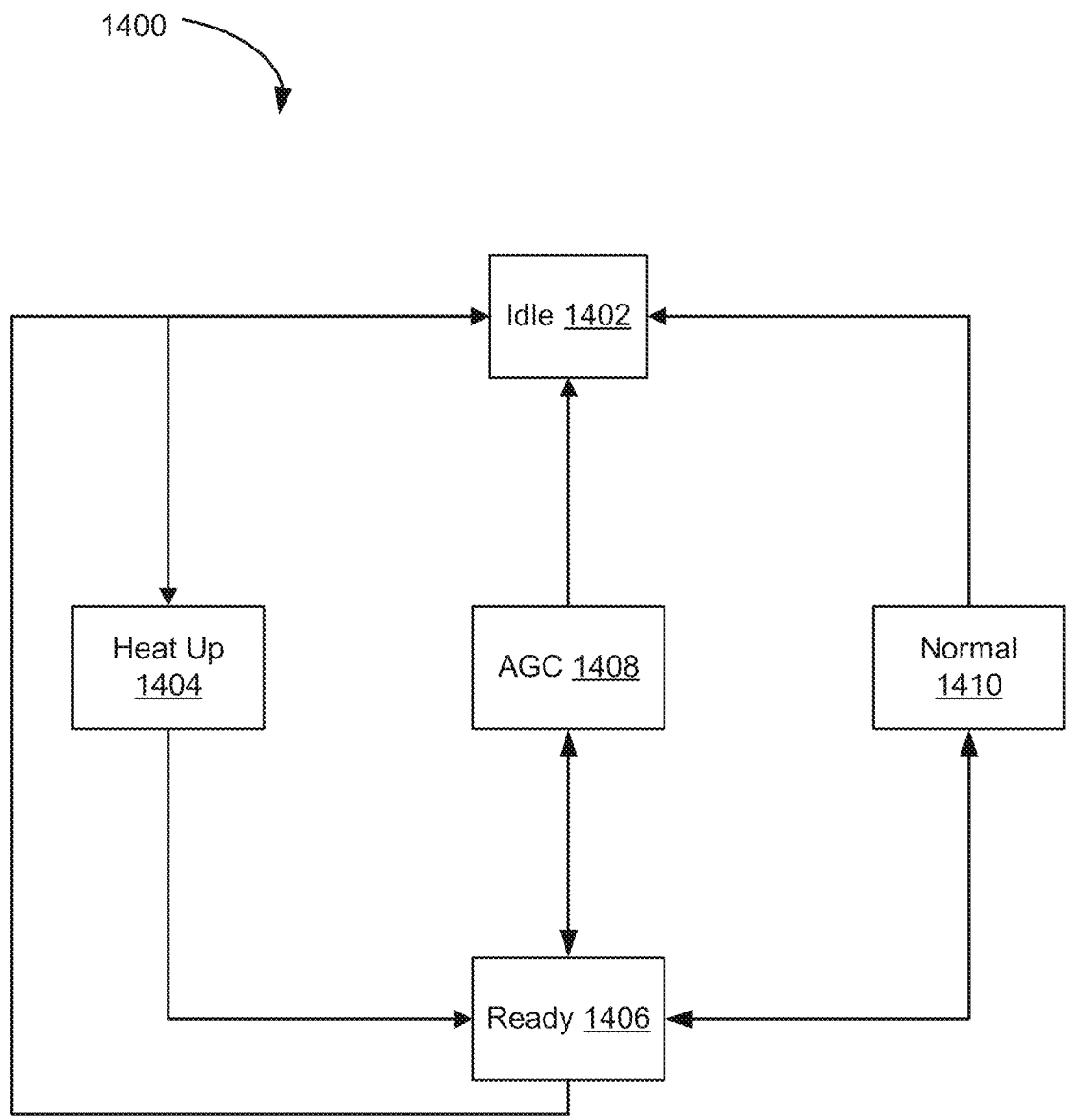
FIG. 14 illustrates an embodiment of a state machine of a millimeter wave radar chip of a sleep monitoring device.

FIG. 14 illustrates an embodiment of a state machine 1400 of a mmwave radar chip of a sleep monitoring device. The sleep monitoring device is an embodiment of the sleep monitoring device 1000 of FIG. 10. The state machine 1400 can be maintained by a radar application, such as the radar application 1120 of FIG. 11, and is usable to control operational state of the mmwave radar chip.

As illustrated, upon the state machine 1400 includes an idle state 1402 applicable to when there is no ongoing sleep session or, if an ongoing sleep session exists, an error has occurred. The mmwave radar chip is not active when the state machine 1400 indicates the idle state 1402 (e.g., if mmwave radar chip was active and the idle state 1402 is entered, the radar application can instruct the mmwave radar chip to deactivate).

Upon a start of a sleep session, a transition occurs from the idle state to a heat up state 1404. Corresponding to the heat up state 1404, the radar application can instruct the mmwave radar chip to perform a heat up process by which the mmwave RF front end and related components are heated up to reach an operational temperature that is within a predefined operational temperature range. Upon the radar application receiving an indication from the mmwave radar chip that the heat up process is complete, a transition is made a ready state 1406. During the ready state 1406, no mmwave RF transmission occurs. Instead, the ready state 1406 is an intermediary state that can be followed by an antenna gain control (AGC) state 1408 to fine tune the RF front end, a normal state 1410 to start the RF transmissions, or the idle state 1402.

If an AGC process has not been performed in the sleep session yet or if the operational temperature falls outside of the operational temperature range, the AGC state 1408 follows the ready state 1406. Corresponding to the AGC state 1408, the radar application instructs the mmwave radar chip to perform the AGC process, whereby the mmwave radar chip adjusts properties of its RF beam (e.g., the beam width). Once complete, a transition to the ready state 1406 is performed. If also the AGC process encountered an error, the ready state 1406 follows the AGC state 1408 and the idle state 1402 follows immediately the ready state 1406.

Corresponding to the normal state 1410, the heat up process and AGC process have been performed and the mmwave RF transmission and reception can be performed. Accordingly, the radar application instructs the mmwave radar chip to transmit mmwave RF signals and process received mmwave RF signals to generate radar data.

If any of the heat up state 1404, AGC state 1408, ready state 1406, or the normal state 1408 is the current state and an event is received indicating an end to the end session, a transition to the idle state 1402 is followed. The transition is direct from the ready state 1406 and indirect, via the ready state 1406, from the heat up state 1404, AGC state 1408, and the normal state 1408. In comparison, if an error occurs and impacts the operations of the mmwave radar chip (e.g., its operational temperature exceeds the operational temperature range or if an API event is received from the mmwave radar chip and indicates a particular error), the transition to the idle state 1406 is performed immediately from any of any of the heat up state 1404, AGC state 1408, ready state 1406, or the normal state 1408.

Figure 15:
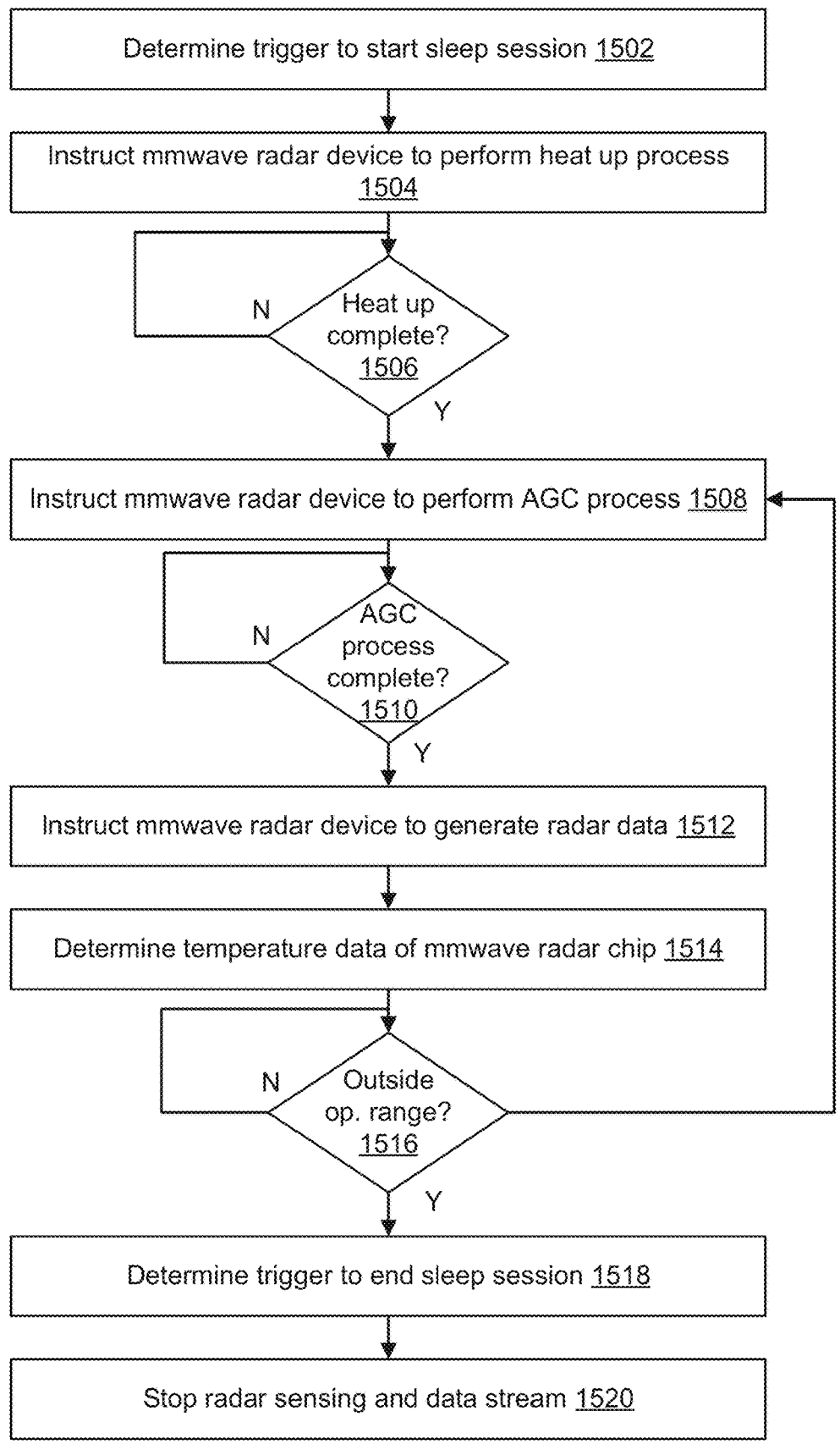
FIG. 15 illustrates an embodiment of a flow for controlling a millimeter wave radar chip of a sleep monitoring device.

FIG. 15 illustrates an embodiment of a flow for controlling a mmwave radar chip of a sleep monitoring device. Operations of the flow can be performed by a processing chip of a sleep monitoring device, such as the processing chip 1100 of FIG. 11, that implements an idle state, a heat up state, a ready state, an AGC state, and a normal state within a state machine. Some or all of the instructions for performing the operations can be implemented as hardware circuitry and/or stored as computer-readable instructions on a non-transitory computer-readable medium of the sleep monitoring device (e.g., as a part of an application module, such as the radar application 1120 of FIG. 11). As implemented, the instructions represent modules that include circuitry or code executable by processor(s) of the sleep monitoring device. The use of such instructions configures the sleep monitoring device to perform the specific operations described herein. Each circuitry or code in combination with the relevant processor(s) represent a means for performing a respective operation(s). While the operations are illustrated in a particular order, it should be understood that no particular order is necessary and that one or more operations may be omitted, skipped, performed in parallel, and/or reordered.

As illustrated, the flow can start at operation 1502, where the sleep monitoring device determines a trigger to start sleep session. This operation can be similar to operation 1302 of FIG. 13. Here additionally, the radar application can receive instruction data from a controller application of the processing chip to activate the mmwave radar chip.

At operation 1504, the sleep monitoring device instructs the mmwave radar device to perform a heat up process. In an embodiment, because the mmwave radar chip has not been activated in the sleep session yet, the radar application determines that the current state from the state machine is the idle state. Accordingly, the radar application sends instruction data (e.g., an API call) to the mmwave radar chip to perform the heat up process, corresponding to the heat up state.

At operation 1506, the sleep monitoring device whether determines the heat up process is complete. For example, the radar application receives status data (e.g., an API response)

indicating that the heat up process is complete. When received, the radar application determines the completion, and operation 1508 follows operation 1506, thereby transitioning to the ready state from the heat up state. Otherwise, no state transition occurs as indicated with the loop back within operation 1506.

At operation 1508, the sleep monitoring device instructs the mmwave radar device to perform an AGC process. In an embodiment, because the current state is the ready state and the mmwave radar chip has not completed an AGC process, the radar application sends instruction data (e.g., an API call) to the mmwave radar chip to perform the AGC process, corresponding to the AGC state.

At operation 1510, the sleep monitoring device whether determines the AGC process is complete. For example, the radar application receives status data (e.g., an API response) indicating that the AGC process is complete. When received, the radar application determines the completion, and operation 1512 follows operation 1508, thereby transitioning to the ready state from the AGC state. Otherwise, no state transition occurs as indicated with the loop back within operation 1510.

At operation 1512, the sleep monitoring device instructs the mmwave radar device to generate radar data. In an embodiment, because the current state is the ready state and the mmwave radar chip has not started the mmwave RF transmission and processing, the radar application sends instruction data (e.g., an API call) to the mmwave radar chip to start transmitting mmwave RF signals and processing received mmwave RF signals, corresponding to the normal state. In response, the mmwave radar chip can generate and send the radar data to the radar application that then passes this data to an uploading application.

At operation 1514, the sleep monitoring device determines temperature data of the mmwave radar chip. For example, the temperature data is data generated by a set of temperature sensors installed within a housing of the sleep monitoring device and indicates an operational temperature of the sleep monitoring device and/or the mmwave radar chip. The temperature data may include the internal temperature of the radar chip or of components of the radar device, where this internal temperature may be generated by a temperature sensor included in the radar chop. The radar application may collect the internal temperature of the radar device or radar chip via an interface between the radar application and the radar chip. The temperature data can be collected by the processing chip.

At operation 1516, the sleep monitoring device determines whether the operational temperature is outside of an operational temperature range. For example, the operational temperature is compared to an upper limit defined for the operational temperature range. If the operational temperature exceeds the upper limit, a transition from the normal state is needed. In the illustrative embodiment of FIG. 15, this transition is back to the ready state (shown with the loop to operation 1508), where the sleep monitoring device can re-start the AGC process. Other transitions are possible and be to the idle state immediately or via the ready state.

The operations 1514 and 1516 relate to the monitoring of a particular error: the operational temperature. These operations can be similarly performed for other types of errors to trigger transitions from the normal state to the idle state as applicable.

At operation 1518, the sleep monitoring device determines a trigger to end the sleep session. This operation can be similar to operation 1314 of FIG. 13. Here additionally, the radar application can receive instruction data from a controller application of the processing chip to deactivate the mmwave radar chip.

At operation 1520, the sleep monitoring device stops render sensing and the data stream. For instance, upon receiving the instruction data from the controller application, the radar application sends a command to the radar chip to stop the mmwave RF transmission and the creation of radar data.

Figure 16:
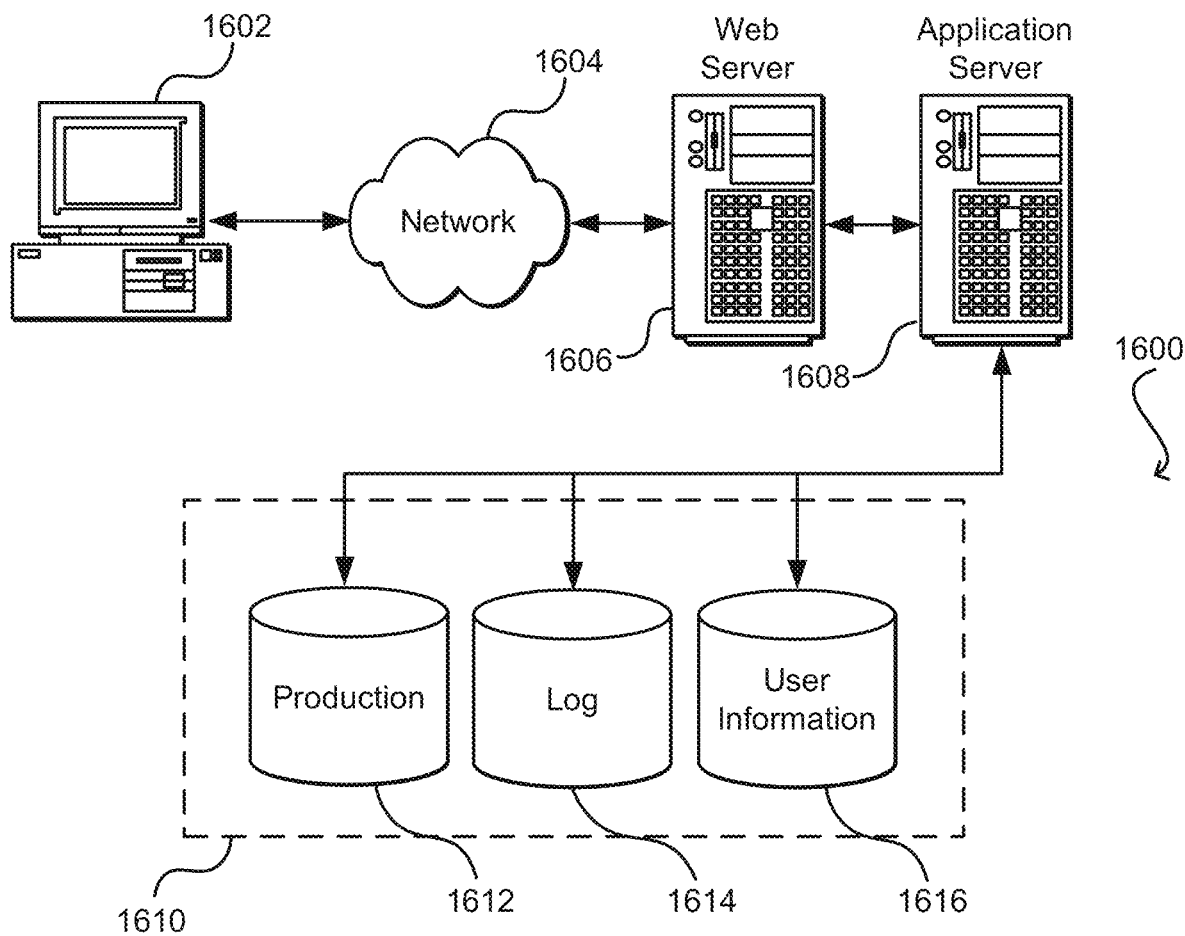
FIG. 16 illustrates aspects of an example environment for implementing aspects in accordance with various embodiments.

FIG. 16 illustrates aspects of an environment for implementing aspects in accordance with various embodiments. This architecture may be used to implement some or all of the computing environments described in connection with FIG. 1. The computer architecture shown in FIG. 16 illustrates a server computer, workstation, desktop computer, laptop, tablet, network appliance, personal digital assistant ("PDA"), e-reader, digital cellular phone, or other computing device (e.g., a sleep monitoring device), and may be utilized to execute any aspects of the software components presented herein.

The computer 1600 includes a baseboard 1602, or "motherboard," which is a printed circuit board to which a multitude of components or devices may be connected by way of a system bus or other electrical communication paths. In one illustrative embodiment, one or more central processing units ("CPUs") 1604 operate in conjunction with a chipset 1606. The CPUs 1604 may be standard programmable processors that perform arithmetic and logical operations necessary for the operation of the computer 1600.

The CPUs 1604 perform operations by transitioning from one discrete, physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits, including registers, adders-subtractors, arithmetic logic units, floating-point units, and the like.

The chipset 1606 provides an interface between the CPUs 1604 and the remainder of the components and devices on the baseboard 1602. The chipset 1606 may provide an interface to a random access memory ("RAM") 1608, used as the main memory in the computer 1600. The chipset 1606 may further provide an interface to a computer-readable storage medium such as a read-only memory ("ROM") 1610 or non-volatile RAM ("NVRAM") for storing basic routines that help to startup the computer 1600 and to transfer information between the various components and devices. The ROM 1610 or NVRAM may also store other software components necessary for the operation of the computer 1600 in accordance with the embodiments described herein.

The computer 1600 may operate in a networked environment using logical connections to remote computing devices and computer systems through a network, such as the local area network 1620. The chipset 1606 may include functionality for providing network connectivity through a NIC 1612, such as a gigabit Ethernet adapter. The NIC 1612 is capable of connecting the computer 1600 to other computing devices over the network 1620. It should be appreciated that multiple NICs 1612 may be present in the computer 1600, connecting the computer to other types of networks and remote computer systems.

The computer 1600 may be connected to a mass storage device 1618 that provides non-volatile storage for the computer. The mass storage device 1618 may store system programs, application programs, other program modules, and data, which have been described in greater detail herein. The mass storage device 1618 may be connected to the computer 1600 through a storage controller 1614 connected to the chipset 1606. The mass storage device 1618 may consist of one or more physical storage units. The storage controller 1614 may interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computer 1600 may store data on the mass storage device 1618 by transforming the physical state of the physical storage units to reflect the information being stored. The specific transformation of physical state may depend on various factors, in different implementations of this description. Examples of such factors may include, but are not limited to, the technology used to implement the physical storage units, whether the mass storage device 1618 is characterized as primary or secondary storage, and the like.

For example, the computer 1600 may store information to the mass storage device 1618 by issuing instructions through the storage controller 1614 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing embodiments provided only to facilitate this description. The computer 1600 may further read information from the mass storage device 1618 by detecting the physical states or characteristics of one or more particular locations within the physical storage units.

In addition to the mass storage device 1618 described above, the computer 1600 may have access to other computer-readable storage media to store and retrieve information, such as program modules, data structures, or other data. It should be appreciated by those skilled in the art that computer-readable storage media can be any available media that provides for the storage of non-transitory data and that may be accessed by the computer 1600.

By way of example, and not limitation, computer-readable storage media may include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

The mass storage device 1618 may store an operating system 1630 utilized to control the operation of the computer 1600. According to one embodiment, the operating system comprises the LINUX operating system. According to another embodiment, the operating system comprises the WINDOWS® SERVER operating system from MICROSOFT Corporation. According to further embodiments, the operating system may comprise the UNIX or SOLARIS operating systems. It should be appreciated that other operating systems may also be utilized. The mass storage device 1618 may store other system or application programs and data utilized by the computer 1600. The mass storage device 1618 might also store other programs and data not specifically identified herein.

In one embodiment, the mass storage device 1618 or other computer-readable storage media is encoded with computer-executable instructions which, when loaded into the computer 1600, transforms the computer from a general-purpose computing system into a special-purpose computer capable of implementing the embodiments described herein. These computer-executable instructions transform the computer 1600 by specifying how the CPUs 1604 transition between states, as described above. According to one embodiment, the computer 1600 has access to computer-readable storage media storing computer-executable instructions which, when executed by the computer 1600, perform the various routines described above. The computer 1600 might also include computer-readable storage media for performing any of the other computer-implemented operations described herein.

The computer 1600 may also include one or more input/output controllers 1616 for receiving and processing input from a number of input devices, such as a keyboard, a mouse, a touchpad, a touch screen, an electronic stylus, or other type of input device. Similarly, the input/output controller 1616 may provide output to a display, such as a computer monitor, a flat-panel display, a digital projector, a printer, a plotter, or other type of output device. It will be appreciated that the computer 1600 may not include all of the components shown in FIG. 16, may include other components that are not explicitly shown in FIG. 16, or may utilize an architecture completely different than that shown in FIG. 16. It should also be appreciated that many computers, such as the computer 1600, might be utilized in combination to embody aspects of the various technologies disclosed herein.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all embodiments, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. A device comprising:
    a housing comprising a first side and an opposing second side;
    a radome transparent to millimeter wave radio frequency (RF) signals and disposed in the first side;
    a radar device comprising a circuit board, a millimeter wave radar signal emitter disposed on the circuit board, and an antenna array, the radar device having a third side and an opposing fourth side, wherein:
        the radar device is positioned at a distance from the radome and is oriented in a plane that is parallel to a plane along which the radome is oriented, the third side facing the radome,
        the antenna array is disposed on the third side and is at a non-zero angle relative to a vertical axis of the device,
        an edge of the circuit board is at a non-zero angle relative to an axis that is normal to a supporting surface on which the housing is supported, and
        the radar device generates radar data based at least in part on reflected millimeter wave RF signals received at the antenna array;
    a main logic board communicatively coupled with the radar device,
    positioned adjacent to the fourth side, and configured to receive the radar data;
    a heat sink positioned adjacent to the main logic board such that the main logic board is between the heat sink and the radar device;
    a clamp positioned between the heat sink and the second side of the housing; and
    a stand coupled with the clamp.

2. The device of claim 1, wherein the radome defines a front surface of the housing and the housing further comprises a peripheral portion coupled to the radome, wherein the peripheral portion blocks RF signals.

3. The device of claim 1, wherein the clamp is coupled with the stand in a press-fit configuration.

4. The device of claim 3, wherein the clamp is formed of a deformable material and abuts a portion of the housing to define a channel between the clamp and the housing, wherein the channel has a first cross-sectional diameter and a portion of the clamp that couples to the stand has a second cross-sectional diameter greater than the first cross-sectional diameter.

5. The device of claim 1, wherein the main logic board is configured to:
    receive first temperature data indicating a first temperature of the radar device at a first time;
    receive second temperature data indicating a second temperature of the radar device at a second time; and
    send instruction data to the radar device based at least in part on a difference between the first temperature and the second temperature, the instruction data causing the radar device to perform an antenna gain control (AGC) process associated with tuning a gain of the antenna array.

6. The device of claim 1, further comprising a button communicatively coupled with the main logic board and a set of sensors comprising at least one of a temperature sensor or an illumination sensor communicatively coupled with the main logic board, and wherein the main logic board is configured to:
    receive, from the button, first data indicating a start of a sleep session;
    cause, in response to the first data, the radar device to transmit first millimeter wave RF signal in an environment of the device;
    receive a second millimeter wave RF signal corresponding to a reflection of the first millimeter wave RF signal;
    receive, from the radar device, respiratory rate data based at least in part on the second millimeter wave RF signals;
    receive, from the set of sensors, sensor data comprising at least one of temperature data or illumination data related to the environment; and
    store the respiratory rate data and the sensor data.

7. The device of claim 1, wherein the main logic board is configured to:
    receive first data indicating a start of a sleep session;
    cause, based on the first data, the radar device to transmit first millimeter wave RF signals in an environment of the device;
    receive second millimeter wave RF signals corresponding to reflections of the first millimeter wave RF signals;
    receive, from the radar device, radar data based at least in part on the second millimeter wave RF signals;
    determine, based at least in part on the radar data, presence of a human in the environment; and
    determine based on presence of the human and the radar data, respiratory rate data associated with the human.

8. A device comprising:
    a housing;
    a radome transparent to millimeter wave radio frequency (RF) signals and defining at least a portion of a front surface of the housing;
    a radar device comprising (i) a circuit board, (ii) a millimeter wave radar signal emitter, and (iii) an antenna array, wherein the millimeter wave radar signal emitter is disposed on the circuit board;

wherein:
the radar device comprises a first side and an opposing second side and is disposed at a distance from the radome with the first side facing the radome,
the antenna array is disposed on the first side and is at a non-zero angle relative to a vertical axis of the device, and the radar device generates radar data based at least in part on reflected millimeter wave RF signals received at the antenna array;

a main logic board comprising one or more processors communicatively coupled with the radar device and configured to receive the radar data;

a heat sink positioned adjacent to the main logic board on a side opposite the radar device;

a clamp positioned between the heat sink and a back surface of the housing; and a stand coupled with the clamp.

9. The device of claim 8, wherein at least one antenna of the antenna array is disposed at an angle of between thirty to sixty degrees relative to the vertical axis.

10. The device of claim 8, further comprising a temperature sensor communicatively coupled with the main logic board, wherein the one or morm processors perform an antenna gain control (AGC) process to tune a gain of the antenna array in response to data received from the temperature sensor indicative of a change in temperature of the radar device.

11. The device of claim 8, further comprising an ambient light sensor communicatively coupled with the main logic board, wherein ambient light data received from the ambient light sensor is conveyed with the radar data to a remote computing system that generates sleep session data based at least in part on the radar data and the ambient light data.

12. The device of claim 8, further comprising an input mechanism,
wherein the millimeter wave radar signal emitter transmits RF signals in response to operation of the input mechanism.

13. The device of claim 8, wherein the antenna array is disposed in the housing, wherein the heat sink has a shape corresponding to a shape of the front surface and is configured to dissipate heat generated by the radar device during operation.

14. The device of claim 8, wherein the clamp is configured to couple with the stand in a press-fit configuration.

15. A sleep monitoring system comprising:
a housing;
a radome transparent to millimeter wave radio frequency (RF) signals and defining at least a portion of a front surface of the housing;
a circuit board comprising a first side and an opposing second side and disposed at a distance from the radome with the first side facing the radome;
a millimeter wave radar signal emitter coupled to the circuit board;
an antenna array coupled to the circuit board on the first side, the antenna array configured to receive reflected millimeter wave RF signals, wherein at least one antenna of the antenna array is disposed at a non-zero angle relative to a vertical axis;
a main logic board comprising one or more processors communicatively coupled with the millimeter wave radar signal emitter and the antenna array and configured to receive signal data associated with the reflected millimeter wave RF signals and generate corresponding radar data;
a heat sink positioned adjacent to the main logic board on a side opposite the millimeter wave radar signal emitter;
a clamp positioned between the heat sink and a back surface of the housing; and
a stand coupled with the clamp.

16. The sleep monitoring system of claim 15, wherein the housing has (i) a vertical axis extending from a top edge to a bottom edge of the housing and (ii) a first lateral surface transparent to millimeter wave RF signals, and wherein the one or more processors are configured to:
cause the millimeter wave radar signal emitter to transmit first millimeter wave RF signals through the first lateral surface;
receive the radar data comprising second millimeter wave RF signals corresponding to reflections of the first millimeter wave RF signals;
determine, based at least in part on the first millimeter wave RF signals and the second millimeter wave RF signals, respiratory rate data; and
store the respiratory rate data.

17. The sleep monitoring system of claim 16, further comprising one or more sensors communicatively coupled to the main logic board and configured to gather at least one of temperature data, humidity data, or illumination data associated with an ambient environment of the sleep monitoring system, wherein the one or more processors are configured to store sensor data received from the one or more sensors and convey the sensor data and the respiratory rate data to a remote computing system.

18. The sleep monitoring system of claim 15, further comprising:
an input mechanism communicatively coupled to the main logic board; and
a wireless communication device communicatively coupled to the main logic board, wherein the one or more processors cause the millimeter wave radar signal emitter to transmit RF signals in response to an activation signal from the input mechanism and the one or more processors cause the wireless communication device to send the radar data to a remote computing system.

19. The sleep monitoring system of claim 15, wherein the one or more processors are configured to:
cause the millimeter wave radar signal emitter to transmit first millimeter wave RF signals through a first lateral surface;
receive second millimeter wave RF signals corresponding to reflections of the first millimeter wave RF signals;
determine, based at least in part on the first millimeter wave RF signals and the second millimeter wave RF signals, respiratory rate data corresponding to a respiratory rate of an individual; and
store the respiratory rate data.

20. The device of claim 1,
wherein the stand defines an axis of orientation of a front surface of the housing, wherein the radome defines at least a portion of the front surface, and wherein the axis of orientation is the same as the vertical axis such that the antenna array is disposed at the non-zero angle relative to the axis of orientation.

21. The device of claim 1, wherein the millimeter wave radar signal emitter is configured to emit an RF signal having a frequency in a range between 30 GHz and 300

GHz, and wherein the distance between the radar device and the radome is based at least in part on the frequency.

* * * * *

UNITED STATES PATENT AND TRADEMARK OFFICE
CERTIFICATE OF CORRECTION

PATENT NO. : 12,239,456 B1
APPLICATION NO. : 17/224587
DATED : March 4, 2025
INVENTOR(S) : Giovanni Mata Magana et al.

Page 1 of 1

It is certified that error appears in the above-identified patent and that said Letters Patent is hereby corrected as shown below:

In the Claims

Claim 10, Column 31 Line 27:
Delete: "morm"
Add: --more--

Signed and Sealed this
Twenty-fifth Day of November, 2025

John A. Squires
*Director of the United States Patent and Trademark Office*